(12) United States Patent
Galloway et al.

(10) Patent No.: US 9,681,814 B2
(45) Date of Patent: *Jun. 20, 2017

(54) DEVICES AND METHODS FOR REAL-TIME DENOISING OF ELECTROCARDIOGRAMS

(71) Applicant: AliveCOR, Inc., San Francisco, CA (US)

(72) Inventors: Conner Daniel Cross Galloway, San Francisco, CA (US); Alexander Vainius Valys, San Francisco, CA (US); Nicholas Peter Hughes, San Francisco, CA (US); David E. Albert, San Francisco, CA (US)

(73) Assignee: Alivecor, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/975,196

(22) Filed: Dec. 18, 2015

(65) Prior Publication Data

US 2016/0242665 A1    Aug. 25, 2016

Related U.S. Application Data

(63) Continuation of application No. 14/327,742, filed on Jul. 10, 2014, now Pat. No. 9,247,911.
(Continued)

(51) Int. Cl.
*A61B 5/04* (2006.01)
*A61B 5/044* (2006.01)
(Continued)

(52) U.S. Cl.
CPC .......... *A61B 5/04017* (2013.01); *A61B 5/044* (2013.01); *A61B 5/0408* (2013.01); *A61B 5/7203* (2013.01); *A61B 5/7235* (2013.01)

(58) Field of Classification Search
CPC ... A61B 5/04017; A61B 5/0408; A61B 5/044; A61B 5/7203; A61B 5/7235
See application file for complete search history.

(56) References Cited

U.S. PATENT DOCUMENTS

| 3,717,857 A | 2/1973 | Evans |
| 3,731,311 A | 5/1973 | Williams |

(Continued)

FOREIGN PATENT DOCUMENTS

| CH | 675675 A5 | 10/1990 |
| CN | 101828915 A | 9/2010 |

(Continued)

OTHER PUBLICATIONS

Adidas miCoach Pacer Review: Like Nike+, Only Better; printed from website http://gizmodo.com/5479456/adidas• printed on Mar. 4, 2010• 5 pages.

(Continued)

*Primary Examiner* — George Manuel
(74) *Attorney, Agent, or Firm* — Wilson Sonsini Goodrich & Rosati

(57) ABSTRACT

Apparatuses and methods (including methods of using such apparatuses) for de-noising electrocardiograms (ECGs) by manually or automatically adjusting the amount of filtering of an ECG signal. For example, real-time ECG signals may be filtered by combining in a weighted fashion an unfiltered portion of an ECG (or a filtered portion of the same ECG) with the same portion of the ECG that has been filtered. The weighting may be adjusted manually and/or automatically. Also described herein are methods for real-time filtering of ECG signals using a combination of filtering techniques including filtering to correct baseline wander, Savitzky-
(Continued)

Golay denoising, and threshold smoothing. Multiple filtering techniques may be combined in a weighed manner to provide signal de-noising.

22 Claims, 8 Drawing Sheets

Related U.S. Application Data

(60) Provisional application No. 61/844,850, filed on Jul. 10, 2013.

(51) Int. Cl.
*A61B 5/00* (2006.01)
*A61B 5/0408* (2006.01)

(56) References Cited

U.S. PATENT DOCUMENTS

| | | |
|---|---|---|
| 3,768,014 A | 10/1973 | Smith et al. |
| 3,776,228 A | 12/1973 | Semler |
| 3,779,237 A | 12/1973 | Roth et al. |
| 3,779,249 A | 12/1973 | Semler |
| 3,782,367 A | 1/1974 | Hochberg et al. |
| 3,805,227 A | 4/1974 | Lester |
| 3,882,277 A | 5/1975 | DePedro et al. |
| 3,885,552 A | 5/1975 | Kennedy |
| 3,898,984 A | 8/1975 | Mandel et al. |
| 3,909,599 A | 9/1975 | Trott, Jr. et al. |
| 4,027,146 A | 5/1977 | Gilmore |
| 4,045,767 A | 8/1977 | Nishihara et al. |
| 4,083,366 A | 4/1978 | Gombrich et al. |
| 4,095,050 A | 6/1978 | Beachem et al. |
| 4,221,223 A | 9/1980 | Linden |
| 4,230,127 A | 10/1980 | Larson |
| 4,231,031 A | 10/1980 | Crowther et al. |
| 4,250,888 A | 2/1981 | Grosskopf |
| 4,281,664 A | 8/1981 | Duggan |
| 4,295,472 A | 10/1981 | Adams |
| 4,312,358 A | 1/1982 | Barney |
| 4,318,130 A | 3/1982 | Heuer |
| 4,364,397 A | 12/1982 | Citron et al. |
| 4,367,752 A | 1/1983 | Jimenez et al. |
| 4,409,984 A | 10/1983 | Dick |
| 4,531,527 A | 7/1985 | Reinhold, Jr. et al. |
| 4,567,883 A | 2/1986 | Langer et al. |
| 4,572,182 A | 2/1986 | Royse |
| 4,580,250 A | 4/1986 | Kago et al. |
| 4,583,553 A | 4/1986 | Shah et al. |
| 4,622,979 A | 11/1986 | Katchis et al. |
| 4,625,730 A | 12/1986 | Fountain et al. |
| 4,630,204 A | 12/1986 | Mortara |
| 4,803,625 A | 2/1989 | Fu et al. |
| 4,889,131 A | 12/1989 | Salem et al. |
| 4,920,489 A | 4/1990 | Hubelbank et al. |
| 4,938,228 A | 7/1990 | Righter et al. |
| 4,938,229 A | 7/1990 | Bergelson et al. |
| 4,958,641 A | 9/1990 | Digby et al. |
| 4,977,899 A | 12/1990 | Digby et al. |
| 4,981,141 A | 1/1991 | Segalowitz |
| 5,012,814 A | 5/1991 | Mills et al. |
| 5,023,906 A | 6/1991 | Novas |
| 5,025,794 A | 6/1991 | Albert et al. |
| 5,058,597 A | 10/1991 | Onoda et al. |
| 5,090,418 A | 2/1992 | Squires et al. |
| 5,111,396 A | 5/1992 | Mills et al. |
| 5,128,552 A | 7/1992 | Fang et al. |
| 5,136,555 A | 8/1992 | Gardos |
| 5,181,519 A | 1/1993 | Bible |
| 5,181,552 A | 1/1993 | Eiermann |
| 5,191,891 A | 3/1993 | Righter |
| 5,201,321 A | 4/1993 | Fulton |
| 5,218,969 A | 6/1993 | Bredesen et al. |
| 5,226,424 A | 7/1993 | Bible |
| 5,238,001 A | 8/1993 | Gallant et al. |
| D341,659 S | 11/1993 | Homayoun |
| 5,259,387 A | 11/1993 | DePinto |
| 5,289,824 A | 3/1994 | Mills et al. |
| 5,301,679 A | 4/1994 | Taylor |
| 5,304,186 A | 4/1994 | Semler et al. |
| 5,313,953 A | 5/1994 | Yomtov et al. |
| 5,317,269 A | 5/1994 | Mills et al. |
| 5,321,618 A | 6/1994 | Gessman |
| 5,333,616 A | 8/1994 | Mills et al. |
| 5,336,245 A | 8/1994 | Adams et al. |
| 5,337,752 A | 8/1994 | Reeves |
| 5,339,824 A | 8/1994 | Engira |
| 5,343,869 A | 9/1994 | Pross et al. |
| 5,343,870 A | 9/1994 | Gallant et al. |
| 5,348,008 A | 9/1994 | Bornn et al. |
| 5,351,695 A | 10/1994 | Mills et al. |
| 5,360,005 A | 11/1994 | Wilk |
| 5,365,935 A | 11/1994 | Righter et al. |
| 5,410,587 A | 4/1995 | Grunwell |
| 5,417,222 A | 5/1995 | Dempsey et al. |
| 5,433,736 A | 7/1995 | Nilsson |
| 5,452,356 A | 9/1995 | Albert |
| 5,466,246 A | 11/1995 | Silvian |
| 5,467,773 A | 11/1995 | Bergelson et al. |
| 5,481,255 A | 1/1996 | Albert et al. |
| 5,503,158 A | 4/1996 | Coppock et al. |
| 5,518,001 A | 5/1996 | Snell |
| 5,522,396 A | 6/1996 | Langer et al. |
| 5,539,705 A | 7/1996 | Akerman et al. |
| D372,785 S | 8/1996 | Sabri |
| 5,544,661 A | 8/1996 | Davis et al. |
| 5,551,953 A | 9/1996 | Lattin et al. |
| 5,561,712 A | 10/1996 | Nishihara |
| 5,568,448 A | 10/1996 | Tanigushi et al. |
| 5,579,284 A | 11/1996 | May |
| 5,583,758 A | 12/1996 | McIlroy et al. |
| D377,983 S | 2/1997 | Sabri |
| 5,608,723 A | 3/1997 | Felsenstein |
| 5,613,495 A | 3/1997 | Mills et al. |
| 5,634,468 A | 6/1997 | Platt et al. |
| 5,652,570 A | 7/1997 | Lepkofker |
| 5,661,699 A | 8/1997 | Sutton |
| 5,675,325 A | 10/1997 | Taniguchi et al. |
| 5,678,562 A | 10/1997 | Sellers |
| 5,701,894 A | 12/1997 | Cherry et al. |
| 5,704,364 A | 1/1998 | Saltzstein et al. |
| 5,724,025 A | 3/1998 | Tavori |
| 5,730,143 A | 3/1998 | Schwarzberg |
| 5,735,285 A | 4/1998 | Albert et al. |
| 5,742,251 A | 4/1998 | Gerber |
| 5,748,103 A | 5/1998 | Flach et al. |
| 5,764,763 A | 6/1998 | Jensen et al. |
| 5,772,586 A | 6/1998 | Heinonen et al. |
| 5,818,788 A | 10/1998 | Kimura et al. |
| 5,825,718 A | 10/1998 | Ueki et al. |
| 5,827,179 A | 10/1998 | Lichter et al. |
| 5,840,020 A | 11/1998 | Heinonen et al. |
| 5,844,997 A | 12/1998 | Murphy, Jr. |
| 5,861,018 A | 1/1999 | Feierbach |
| 5,873,369 A | 2/1999 | Laniado et al. |
| 5,876,351 A | 3/1999 | Rohde |
| 5,877,675 A | 3/1999 | Rebstock et al. |
| 5,889,730 A | 3/1999 | May |
| 5,908,383 A | 6/1999 | Brynjestad |
| 5,929,761 A | 7/1999 | Van et al. |
| 5,941,829 A | 8/1999 | Saltzstein et al. |
| 5,954,640 A | 9/1999 | Szabo |
| D414,870 S | 10/1999 | Saltzstein |
| 5,970,388 A | 10/1999 | Will |
| 5,976,083 A | 11/1999 | Richardson et al. |
| 5,982,297 A | 11/1999 | Welle |
| 5,983,127 A | 11/1999 | DePinto |
| 6,008,703 A | 12/1999 | Perrott et al. |
| 6,014,631 A | 1/2000 | Teagarden et al. |
| 6,024,699 A | 2/2000 | Surwit et al. |
| 6,024,705 A | 2/2000 | Schlager et al. |
| 6,037,704 A | 3/2000 | Welle |
| 6,039,688 A | 3/2000 | Douglas et al. |

(56) References Cited

U.S. PATENT DOCUMENTS

| | | |
|---|---|---|
| 6,048,319 A | 4/2000 | Hudgins et al. |
| D427,315 S | 6/2000 | Saltzstein |
| 6,072,396 A | 6/2000 | Gaukel |
| 6,083,248 A | 7/2000 | Thompson |
| 6,084,510 A | 7/2000 | Lemelson et al. |
| 6,100,806 A | 8/2000 | Gaukel |
| 6,102,856 A | 8/2000 | Groff et al. |
| 6,126,596 A | 10/2000 | Freedman |
| 6,153,532 A | 11/2000 | Dow et al. |
| 6,159,147 A | 12/2000 | Lichter et al. |
| 6,171,256 B1 | 1/2001 | Joo et al. |
| 6,198,394 B1 | 3/2001 | Jacobsen et al. |
| 6,223,164 B1 | 4/2001 | Seare et al. |
| 6,224,548 B1 | 5/2001 | Gopinathan et al. |
| 6,236,889 B1 | 5/2001 | Soykan et al. |
| 6,264,614 B1 | 7/2001 | Albert et al. |
| 6,282,440 B1 | 8/2001 | Brodnick et al. |
| 6,282,441 B1 | 8/2001 | Raymond et al. |
| 6,289,238 B1 | 9/2001 | Besson et al. |
| 6,319,201 B1 | 11/2001 | Wilk |
| 6,343,049 B1 | 1/2002 | Toda |
| 6,363,139 B1 | 3/2002 | Zurek et al. |
| 6,364,834 B1 | 4/2002 | Reuss et al. |
| 6,366,871 B1 | 4/2002 | Geva |
| 6,377,843 B1 | 4/2002 | Naydenov et al. |
| 6,418,394 B1 | 7/2002 | Puolakanaho et al. |
| 6,433,689 B1 | 8/2002 | Hovind et al. |
| 6,453,164 B1 | 9/2002 | Fuller et al. |
| 6,478,736 B1 | 11/2002 | Mault |
| 6,507,734 B1 | 1/2003 | Berger et al. |
| 6,513,532 B2 | 2/2003 | Mault et al. |
| 6,549,756 B1 | 4/2003 | Engstrom |
| 6,558,320 B1 | 5/2003 | Causey, III et al. |
| 6,579,231 B1 | 6/2003 | Phipps |
| 6,595,929 B2 | 7/2003 | Stivoric et al. |
| 6,600,471 B2 | 7/2003 | Lee et al. |
| 6,605,038 B1 | 8/2003 | Teller et al. |
| 6,612,985 B2 | 9/2003 | Eiffert et al. |
| 6,616,613 B1 | 9/2003 | Goodman |
| 6,636,761 B2 | 10/2003 | Brodnick |
| 6,685,633 B2 | 2/2004 | Albert et al. |
| 6,717,983 B1 | 4/2004 | Toda |
| 6,790,178 B1 | 9/2004 | Mault et al. |
| 6,804,558 B2 | 10/2004 | Haller et al. |
| 6,820,057 B1 | 11/2004 | Loch et al. |
| 6,845,263 B2 | 1/2005 | Kawaguchi |
| 6,893,396 B2 | 5/2005 | Schulze et al. |
| 6,928,535 B2 | 8/2005 | Yamashita et al. |
| 6,950,681 B2 | 9/2005 | Hofmann |
| 6,970,737 B1 | 11/2005 | Brodnick et al. |
| 6,987,965 B2 | 1/2006 | Ng et al. |
| 7,009,511 B2 | 3/2006 | Mazar et al. |
| 7,018,339 B2 | 3/2006 | Birnbaum et al. |
| 7,020,508 B2 | 3/2006 | Stivoric et al. |
| 7,031,745 B2 | 4/2006 | Shen |
| 7,061,381 B2 | 6/2006 | Forcier et al. |
| 7,103,407 B2 | 9/2006 | Hjelt et al. |
| 7,107,095 B2 | 9/2006 | Manolas |
| 7,108,659 B2 | 9/2006 | Ross et al. |
| 7,136,693 B2 | 11/2006 | Brodnick |
| 7,153,262 B2 | 12/2006 | Stivoric et al. |
| 7,162,294 B2 | 1/2007 | Rowlandson et al. |
| 7,171,166 B2 | 1/2007 | Ng et al. |
| 7,188,151 B2 | 3/2007 | Kumar et al. |
| 7,215,991 B2 | 5/2007 | Besson et al. |
| 7,222,054 B2 | 5/2007 | Geva |
| 7,236,818 B2 | 6/2007 | McLeod et al. |
| 7,257,448 B2 | 8/2007 | Crowe et al. |
| 7,260,429 B2 | 8/2007 | Siejko et al. |
| 7,261,690 B2 | 8/2007 | Teller et al. |
| 7,285,090 B2 | 10/2007 | Stivoric et al. |
| 7,319,425 B2 | 1/2008 | Fiorenza et al. |
| 7,324,836 B2 | 1/2008 | Steenstra et al. |
| RE40,116 E | 2/2008 | Engstrom |
| 7,349,574 B1 | 3/2008 | Sodini et al. |
| 7,351,207 B2 | 4/2008 | Priemer |
| 7,354,400 B2 | 4/2008 | Asafusa et al. |
| 7,383,297 B1 | 6/2008 | Atsmon et al. |
| 7,415,304 B2 | 8/2008 | Rowlandson et al. |
| 7,444,116 B2 | 10/2008 | Ivanov et al. |
| 7,509,159 B2 | 3/2009 | Xue et al. |
| 7,520,860 B2 | 4/2009 | Guion-Johnson et al. |
| 7,542,878 B2 | 6/2009 | Nanikashvili |
| 7,548,623 B2 | 6/2009 | Manabe |
| 7,552,081 B2 | 6/2009 | Dutta et al. |
| 7,596,405 B2 | 9/2009 | Kurzweil et al. |
| 7,603,148 B2 | 10/2009 | Michalak |
| 7,654,148 B2 | 2/2010 | Tomlinson, Jr. et al. |
| 7,657,479 B2 | 2/2010 | Henley |
| 7,668,589 B2 | 2/2010 | Bauer |
| 7,689,437 B1 | 3/2010 | Teller et al. |
| 7,701,895 B2 | 4/2010 | Gehasie et al. |
| 7,733,224 B2 | 6/2010 | Tran |
| 7,742,808 B2 | 6/2010 | Nissila et al. |
| 7,819,814 B2 | 10/2010 | Gavriely et al. |
| 7,846,104 B2 | 12/2010 | MacQuarrie et al. |
| 7,846,106 B2 | 12/2010 | Andrews et al. |
| 7,904,160 B2 | 3/2011 | Brodnick et al. |
| 7,945,064 B2 | 5/2011 | O'Brien et al. |
| 7,945,462 B1 | 5/2011 | Goral |
| 7,946,959 B2 | 5/2011 | Shum et al. |
| 7,955,273 B2 | 6/2011 | Rahe-Meyer |
| 7,983,749 B2 | 7/2011 | Warren |
| 8,019,609 B2 | 9/2011 | Tamir et al. |
| 8,034,006 B2 | 10/2011 | Celik-Butler et al. |
| 8,062,090 B2 | 11/2011 | Atsmon et al. |
| 8,073,707 B2 | 12/2011 | Teller et al. |
| 8,078,136 B2 | 12/2011 | Atsmon et al. |
| 8,078,278 B2 | 12/2011 | Penner |
| 8,109,874 B2 | 2/2012 | Kong et al. |
| 8,126,566 B2 | 2/2012 | Stahmann et al. |
| 8,126,728 B2 | 2/2012 | Dicks et al. |
| 8,130,093 B2 | 3/2012 | Mazar et al. |
| 8,150,750 B2 | 4/2012 | Ray |
| 8,160,276 B2 | 4/2012 | Liao et al. |
| 8,165,677 B2 | 4/2012 | Von et al. |
| 8,224,429 B2 | 7/2012 | Prstojevich et al. |
| 8,265,907 B2 | 9/2012 | Nanikashvili et al. |
| 8,275,635 B2 | 9/2012 | Stivoric et al. |
| 8,282,550 B2 | 10/2012 | Rasdal et al. |
| 8,285,356 B2 | 10/2012 | Bly et al. |
| 8,301,232 B2 | 10/2012 | Albert et al. |
| 8,301,236 B2 | 10/2012 | Baumann et al. |
| 8,315,695 B2 | 11/2012 | Sebelius et al. |
| 8,323,188 B2 | 12/2012 | Tran |
| 8,328,718 B2 | 12/2012 | Tran |
| 8,332,233 B2 | 12/2012 | Ott et al. |
| 8,364,250 B2 | 1/2013 | Moon et al. |
| 8,369,936 B2 | 2/2013 | Farringdon et al. |
| 8,374,688 B2 | 2/2013 | Libbus et al. |
| 8,449,471 B2 | 5/2013 | Tran |
| 8,500,636 B2 | 8/2013 | Tran |
| 8,509,882 B2 | 8/2013 | Albert et al. |
| 8,519,835 B2 | 8/2013 | Dunko |
| 8,525,673 B2 | 9/2013 | Tran |
| 8,543,185 B2 | 9/2013 | Yuen et al. |
| 8,543,351 B2 | 9/2013 | Yuen et al. |
| 8,547,248 B2 | 10/2013 | Zdeblick et al. |
| 8,548,770 B2 | 10/2013 | Yuen et al. |
| 8,583,402 B2 | 11/2013 | Yuen et al. |
| 8,684,900 B2 | 4/2014 | Tran |
| 8,700,137 B2 | 4/2014 | Albert |
| 9,220,430 B2 | 12/2015 | Albert |
| 2001/0025139 A1 | 9/2001 | Pearlman |
| 2001/0027384 A1 | 10/2001 | Schulze et al. |
| 2001/0031998 A1 | 10/2001 | Nelson et al. |
| 2001/0051766 A1 | 12/2001 | Gazdzinski |
| 2002/0016541 A1 | 2/2002 | Glossop |
| 2002/0032386 A1 | 3/2002 | Sackner et al. |
| 2002/0065758 A1 | 5/2002 | Henley |
| 2002/0082665 A1 | 6/2002 | Haller et al. |
| 2002/0111556 A1 | 8/2002 | Wegner |
| 2002/0143576 A1 | 10/2002 | Nolvak et al. |
| 2003/0004425 A1 | 1/2003 | Narimatsu et al. |

(56) References Cited

U.S. PATENT DOCUMENTS

| | | |
|---|---|---|
| 2003/0093002 A1 | 5/2003 | Kuo |
| 2003/0097153 A1 | 5/2003 | Bardy et al. |
| 2003/0107487 A1 | 6/2003 | Korman et al. |
| 2003/0117987 A1 | 6/2003 | Brebner |
| 2003/0149344 A1 | 8/2003 | Nizan |
| 2003/0193839 A1 | 10/2003 | Singh |
| 2004/0002662 A1 | 1/2004 | Hjelt et al. |
| 2004/0010201 A1 | 1/2004 | Korzinov et al. |
| 2004/0034284 A1 | 2/2004 | Aversano et al. |
| 2004/0044292 A1 | 3/2004 | Yasushi et al. |
| 2004/0059205 A1 | 3/2004 | Carlson et al. |
| 2004/0093331 A1 | 5/2004 | Garner et al. |
| 2004/0117212 A1 | 6/2004 | Kong et al. |
| 2004/0143403 A1 | 7/2004 | Brandon et al. |
| 2004/0215088 A1 | 10/2004 | Hubelbank |
| 2004/0215094 A1 | 10/2004 | Baumer et al. |
| 2004/0220487 A1 | 11/2004 | Vyshedskiy et al. |
| 2004/0220488 A1 | 11/2004 | Vyshedskiy et al. |
| 2004/0225199 A1 | 11/2004 | Evanyk et al. |
| 2004/0228217 A1 | 11/2004 | Szeto |
| 2004/0236379 A1 | 11/2004 | Bardy et al. |
| 2004/0236819 A1 | 11/2004 | Anati et al. |
| 2004/0266407 A1 | 12/2004 | Lee et al. |
| 2004/0266480 A1 | 12/2004 | Hjelt et al. |
| 2005/0014531 A1 | 1/2005 | Findikli |
| 2005/0027207 A1 | 2/2005 | Westbrook et al. |
| 2005/0078533 A1 | 4/2005 | Vyshedskiy et al. |
| 2005/0124864 A1 | 6/2005 | Mack et al. |
| 2005/0234353 A1 | 10/2005 | Xue et al. |
| 2006/0022833 A1 | 2/2006 | Ferguson et al. |
| 2006/0047215 A1 | 3/2006 | Newman et al. |
| 2006/0173259 A1 | 8/2006 | Flaherty et al. |
| 2006/0190045 A1 | 8/2006 | Marcus et al. |
| 2006/0224051 A1 | 10/2006 | Teller et al. |
| 2006/0252999 A1 | 11/2006 | Devaul et al. |
| 2007/0021677 A1 | 1/2007 | Markel |
| 2007/0027386 A1 | 2/2007 | Such et al. |
| 2007/0032731 A1 | 2/2007 | Lovejoy et al. |
| 2007/0032733 A1 | 2/2007 | Burton |
| 2007/0063850 A1 | 3/2007 | Devaul et al. |
| 2007/0106179 A1 | 5/2007 | Bagha et al. |
| 2007/0156060 A1 | 7/2007 | Cervantes et al. |
| 2007/0254604 A1 | 11/2007 | Kim |
| 2007/0265038 A1 | 11/2007 | Kim |
| 2008/0009759 A1 | 1/2008 | Chetham et al. |
| 2008/0058670 A1 | 3/2008 | Mainini |
| 2008/0097537 A1 | 4/2008 | Duann et al. |
| 2008/0112885 A1 | 5/2008 | Okunev et al. |
| 2008/0146890 A1 | 6/2008 | LeBoeuf et al. |
| 2008/0171945 A1 | 7/2008 | Dotter |
| 2008/0177162 A1 | 7/2008 | Bae et al. |
| 2008/0198872 A1 | 8/2008 | Pierce |
| 2008/0214903 A1 | 9/2008 | Orbach |
| 2008/0221632 A1 | 9/2008 | Bardy et al. |
| 2008/0228045 A1 | 9/2008 | Gao et al. |
| 2008/0293453 A1 | 11/2008 | Atlas et al. |
| 2009/0010461 A1 | 1/2009 | Klinghult et al. |
| 2009/0024045 A1 | 1/2009 | Prakash et al. |
| 2009/0037575 A1 | 2/2009 | Crystal et al. |
| 2009/0117883 A1 | 5/2009 | Coffing et al. |
| 2009/0144080 A1 | 6/2009 | Gray et al. |
| 2009/0149767 A1 | 6/2009 | Rossetti |
| 2009/0156908 A1 | 6/2009 | Belalcazar et al. |
| 2009/0171170 A1 | 7/2009 | Li et al. |
| 2009/0209873 A1 | 8/2009 | Pinter et al. |
| 2009/0273467 A1 | 11/2009 | Elixmann et al. |
| 2009/0279389 A1 | 11/2009 | Irie |
| 2009/0287067 A1 | 11/2009 | Dorogusker et al. |
| 2009/0312655 A1 | 12/2009 | Lo |
| 2010/0027379 A1 | 2/2010 | Saulnier et al. |
| 2010/0033303 A1 | 2/2010 | Dugan et al. |
| 2010/0035927 A1 | 2/2010 | Ojika et al. |
| 2010/0042008 A1 | 2/2010 | Amitai et al. |
| 2010/0049006 A1 | 2/2010 | Magar et al. |
| 2010/0049037 A1 | 2/2010 | Pinter et al. |
| 2010/0063381 A1 | 3/2010 | Greiser |
| 2010/0069735 A1 | 3/2010 | Berkner |
| 2010/0076276 A1 | 3/2010 | Gilland |
| 2010/0094152 A1 | 4/2010 | Semmlow |
| 2010/0113950 A1 | 5/2010 | Lin et al. |
| 2010/0148956 A1 | 6/2010 | Song et al. |
| 2010/0152598 A1 | 6/2010 | Zhang |
| 2010/0184479 A1 | 7/2010 | Griffin, Jr. |
| 2010/0204758 A1 | 8/2010 | Boon et al. |
| 2010/0208434 A1 | 8/2010 | Kim et al. |
| 2010/0217099 A1 | 8/2010 | Leboeuf et al. |
| 2010/0217100 A1 | 8/2010 | Leboeuf et al. |
| 2010/0217144 A1 | 8/2010 | Brian |
| 2010/0217345 A1 | 8/2010 | Wolfe et al. |
| 2010/0256509 A1 | 10/2010 | Kuo et al. |
| 2010/0281261 A1 | 11/2010 | Razzell |
| 2010/0298711 A1 | 11/2010 | Pedersen et al. |
| 2010/0324378 A1 | 12/2010 | Tran et al. |
| 2010/0331631 A1 | 12/2010 | MacLaughlin |
| 2011/0004110 A1 | 1/2011 | Shusterman |
| 2011/0015496 A1 | 1/2011 | Sherman et al. |
| 2011/0035927 A1 | 2/2011 | Griffin et al. |
| 2011/0066042 A1 | 3/2011 | Pandia et al. |
| 2011/0117529 A1 | 5/2011 | Barash et al. |
| 2011/0134725 A1 | 6/2011 | Su et al. |
| 2011/0152957 A1 | 6/2011 | Shaquer |
| 2011/0160601 A1 | 6/2011 | Wang et al. |
| 2011/0235466 A1 | 9/2011 | Booij et al. |
| 2011/0301439 A1 | 12/2011 | Albert et al. |
| 2011/0319949 A1 | 12/2011 | Bardy et al. |
| 2012/0051187 A1 | 3/2012 | Paulson et al. |
| 2012/0053424 A1 | 3/2012 | Kenalty et al. |
| 2012/0071734 A1 | 3/2012 | Shimuta et al. |
| 2012/0116240 A1 | 5/2012 | Chou |
| 2012/0123232 A1 | 5/2012 | Najarian et al. |
| 2012/0123285 A1 | 5/2012 | Zhang |
| 2012/0123891 A1 | 5/2012 | Patel |
| 2012/0127833 A1 | 5/2012 | Ghen et al. |
| 2012/0136264 A1 | 5/2012 | Zhang |
| 2012/0143018 A1 | 6/2012 | Skidmore et al. |
| 2012/0147921 A1 | 6/2012 | Conti et al. |
| 2012/0157019 A1 | 6/2012 | Li |
| 2012/0157802 A1 | 6/2012 | Chou |
| 2012/0157865 A1* | 6/2012 | Stein .............. A61B 5/04014 600/509 |
| 2012/0158090 A1 | 6/2012 | Chavan et al. |
| 2012/0171963 A1 | 7/2012 | Tsfaty |
| 2012/0179056 A1 | 7/2012 | Moulder et al. |
| 2012/0203124 A1 | 8/2012 | Lim |
| 2012/0221476 A1 | 8/2012 | Candelario |
| 2012/0316413 A1 | 12/2012 | Liu et al. |
| 2013/0030259 A1 | 1/2013 | Thomsen et al. |
| 2013/0046162 A1 | 2/2013 | Baumann et al. |
| 2013/0085364 A1 | 4/2013 | Lu et al. |
| 2013/0197320 A1 | 8/2013 | Albert et al. |
| 2013/0236980 A1 | 9/2013 | Moretti et al. |
| 2013/0261414 A1 | 10/2013 | Tal et al. |
| 2013/0331663 A1 | 12/2013 | Albert et al. |
| 2013/0338460 A1 | 12/2013 | He et al. |
| 2014/0050321 A1 | 2/2014 | Albert et al. |
| 2014/0128758 A1 | 5/2014 | Galloway et al. |
| 2014/0222097 A1 | 8/2014 | Bardy et al. |
| 2014/0276162 A1 | 9/2014 | Albert et al. |
| 2015/0018702 A1 | 1/2015 | Galloway et al. |
| 2016/0249823 A1 | 9/2016 | Galloway et al. |

FOREIGN PATENT DOCUMENTS

| | | |
|---|---|---|
| CN | 201918016 U | 8/2011 |
| CN | 102347804 A | 2/2012 |
| DE | 2506936 A1 | 9/1976 |
| DE | 4212670 A1 | 1/1994 |
| EP | 0631226 A1 | 12/1994 |
| EP | 0980227 A1 | 2/2000 |
| EP | 1407713 A1 | 4/2004 |
| EP | 1181888 B1 | 9/2007 |
| EP | 1238633 B1 | 10/2008 |
| EP | 2030565 A1 | 3/2009 |
| EP | 2116183 B1 | 2/2012 |

(56) References Cited

FOREIGN PATENT DOCUMENTS

| | | |
|---|---|---|
| FR | 2740426 A1 | 4/1997 |
| GB | 2181554 A | 4/1987 |
| GB | 2408105 A | 5/2005 |
| JP | S59122032 A | 7/1984 |
| JP | S59190742 A | 10/1984 |
| JP | S63072231 A | 4/1988 |
| JP | S63294044 A | 11/1988 |
| JP | H01244328 A | 9/1989 |
| JP | H05167540 A | 7/1993 |
| JP | H06326669 A | 11/1994 |
| JP | 2002191562 A | 7/2002 |
| JP | 2002261731 A | 9/2002 |
| JP | 2003010177 A | 1/2003 |
| JP | 2005295378 A | 10/2005 |
| JP | 2012065073 A | 3/2012 |
| MX | 2009011781 A | 5/2011 |
| WO | WO-8200910 A1 | 3/1982 |
| WO | WO-8805282 A1 | 7/1988 |
| WO | WO-9008361 A1 | 7/1990 |
| WO | WO-9206551 A1 | 4/1992 |
| WO | WO-9731437 A1 | 8/1997 |
| WO | WO-9838611 A1 | 9/1998 |
| WO | WO-9838909 A1 | 9/1998 |
| WO | WO-9858338 A2 | 12/1998 |
| WO | WO-9904043 A1 | 1/1999 |
| WO | WO-9944494 A1 | 9/1999 |
| WO | WO-0041620 A1 | 7/2000 |
| WO | WO-0147597 A2 | 7/2001 |
| WO | WO-0157619 A2 | 8/2001 |
| WO | WO-0233846 A1 | 4/2002 |
| WO | WO-02080762 A1 | 10/2002 |
| WO | WO-03075118 A2 | 9/2003 |
| WO | WO-03094720 A1 | 11/2003 |
| WO | WO-2004037080 A1 | 5/2004 |
| WO | WO-2005124864 A1 | 12/2005 |
| WO | WO-2006001005 A2 | 1/2006 |
| WO | WO-2006021956 A2 | 3/2006 |
| WO | WO-2007014545 A2 | 2/2007 |
| WO | WO-2007088315 A1 | 8/2007 |
| WO | WO-2008005015 A1 | 1/2008 |
| WO | WO-2008066682 A2 | 6/2008 |
| WO | WO-2010025166 A1 | 3/2010 |
| WO | WO-2010108287 A1 | 9/2010 |
| WO | WO-2010113354 A1 | 10/2010 |
| WO | WO-2010144626 A1 | 12/2010 |
| WO | WO-2011006356 A1 | 1/2011 |
| WO | WO-2011008838 A1 | 1/2011 |
| WO | WO-2011014292 A1 | 2/2011 |
| WO | WO-2011022942 A1 | 3/2011 |
| WO | WO-2011040877 A1 | 4/2011 |
| WO | WO-2011040878 A1 | 4/2011 |
| WO | WO-2011113070 A1 | 9/2011 |
| WO | WO-2011137375 A2 | 11/2011 |
| WO | WO-2012046158 A1 | 4/2012 |
| WO | WO-2012108895 A1 | 8/2012 |
| WO | WO-2012129413 A1 | 9/2012 |
| WO | WO-2012160550 A1 | 11/2012 |
| WO | WO-2013036307 A1 | 3/2013 |
| WO | WO-2013066642 A1 | 5/2013 |
| WO | WO-2013093690 A1 | 6/2013 |
| WO | WO-2013122788 A1 | 8/2013 |
| WO | WO-2013138500 A1 | 9/2013 |
| WO | WO-2013155196 A2 | 10/2013 |
| WO | WO-2013192166 A1 | 12/2013 |

OTHER PUBLICATIONS

Australian Design Awards. Heartplus Micro; printed from website http://www.designawards.com/au; printed on Apr. 12, 2002 • 6 pages.
Bajaj, M.D.; "Event Recording in Ambulatory Patients with Syncopal Events"; University of Kansas; Wichita, Kansas; (no date); pp. 15-18; printed on or before Apr. 14, 2010.
Bluetooth. Headset Profile (HSP), printed from website http://bluetooth.com/English/Techmology/Works/Pates/HSP.asgx, printed on May 12, 2010.
Bramanti et al., Multichannel telemetric system for biomedical signals via switched telephone lines, Medical and Biological Engineering and Computing, Sep. 1982, vol. 20, No. 5, pp. 653-656.
Burke, "A Micropower Dry-Electrode ECG Preamplifier", IEEE Transactions on Biomedical Engineering, Feb. 2000, vol. 47, No. 2, pp. 155-162.
Card Guard CG-6108 ACT Ambulatory Cardiac Telemetry Brochure; Card Guard; The Telemedicine Company: Switzerland; 2006; 2 pages.
Cardiocomm Solutions; Gems Air. (PC based ECG management) printed from website http://www.cardiocommsolutions/com; printed on Mar. 19, 2010; 1 page.
Charuvastra. Transtelephonic Cardiac Event Recording for Arrhythmia Surveillance; printed from website http://tchin.org/resource room/c art• printed on Mar. 26, 2010• 2 pages.
Cheng, Allen C.; "Real-Time Cardiovascular Diseases Detection on a Smartphone"; Departments of Electrical and Computer Engineering, Bioengineering, Neurological Surgery and Computer Science; University of Pittsburgh; Pittsburgh, PA; printed on or before Apr. 14, 2010.
Company-Bosch et al.; ECG Front-End Design is Simplified with MicroConverter; Analog Dialogue; Nov. 2003; vol. 37(11); pp. 1-5.
Creative. PC-80B Portable ECG Monitor w/sd card extension slot; printed from website www.amazon.com/Portable-Monitor-extension-leather-shipping/dp/B0010jWKUE; printed on Feb. 4, 2010• 5 pages.
Deveau, "Health Care eyes smart phones to heal ills", printed from the website http://www.theQiobeandmail.com on Sep. 17, 2009, 4 pages.
Dinh. Heart activity monitoring on smartphone. IPCBEE—Int conf Biomedical Eng and Technol. Jun. 17-19, 2011. 11:45-49.
Dobrev, et al., Bootstrapped two-electrode biosignal amplifier, Med Bioi Eng Comput, 2008, 7 pages.
Dolan. FDA promises regulatory guidance this year. Mobihealthnews. Mar. 17, 2011. (http://mobihealthnews.com/10495/fda-promises-regulatory-guidance-this-year/).
Dolan; Qualcomm launches ECG smartphone program in China; Sep. 8, 2011; 11 pgs.; retrieved Mar. 19, 2014 from the internet (http://mobihealthnews.com/13092/qualcomm-launches-ecg-smartphone-program-in-china/).
Dower, et al. Time-selective filtering for computerized electrocardiography. Computers in Cardiology. Sep. 1979; 267-270.
Elert, Glenn (Editor); Frequency Range of Human Hearing; The Physics Factbook; web version as of Mar. 29, 2010; 2 pgs.; printed Jun. 6, 2012 (http://web.archive.org/web/20100329141847/http:I/hypertextbook.com/facts/2003/ChrisDAmbrose.shtml).
F. N. Fritsch and R. E. Carlson, Monotone Piecewise Cubic Interpolation, SIAM Journal on Numerical Analysis, 17: 238-246 (1980).
Fausti-Flora, et al. Data Critical's RhythmStat XL Technology Receives FDA Clearance Bringing a Revolutionary Wireless Solution to the Telemedicine Marketplace. Business Wire. Dec. 11, 1997.
Favorite Plus. Handheld Easy ECG Monitor—Handheld Easy EKG Monitor; printed from website www.favoriteplus.com/easy-ecg-handgeld-monitor-fp; printed on Feb. 4, 2010; 2 pages.
Favorite Plus. Handheld ECG Monitor—Handheld EKG Monitor at Favoriteplus.com; printed from website www.favoriteplus.com/handheld-ecg-ekg-monitor; printed on Feb. 4, 2010; 3 pages.
Favorite Plus. Handheld ECG Monitor—Handheld EKG Monitor InstantCheck; printed from website http://www. favoriteplus.com/instanchcheck-hand held-ecg-ekg-monitor; printed on Feb. 4, 2010; 2 pages.
Ferrick, M.D.; "Holter Monitoring and cardiac Event Recording in Assessing Symptomatic Patients"; Albert Einstein College of Medicine; Bronx, New York; (no date)• pp. 11-14• printed on or before Apr. 14, 2010.
Free2move. Vitaphone 2300; www.free2move.us/News/NewsVitaghone 240105.htm printed May 12, 2010.

(56) References Cited

OTHER PUBLICATIONS

Fulford-Jones, et al., "A Portable, Low-Power, Wireless Two-Lead EKG System", Division of Engineering and Applied Sciences, Harvard University, Sep. 2004, 4 pages.
Garabelli et al. Accuracy and Novelty of an Inexpensive iPhone-based Event Recorder (Presentation Poster/Abstract) Heart Rhythm 2012, 33rd Annual Scientific Session. SP23. Innovation Poster Session II. No. IA02-1; May 11, 2012.
GBI Portal. Qualcomm's wireless reach mHealth project to improve cardiovascular disease in resource scarce China; Feb. 17, 2012; 7 pgs. Retrieved Mar. 19, 2014 from www.intergrallc.com/2012/02/17/qualcooms-wireless-reach-mhealth-project-to-improve-cardio-vascular-disease-in-resource-scarce-china/.
Gillette, M.D.; "Diagnosis of Pediatric Arrhythmias with Event Recording"; Medical University of South Carolina; Charleston, South Carolina; (no date); pp. 25-32; printed on or before Apr. 14, 2010.
Grier, James W.; "How to use 1-lead ECG recorders to obtain 12-lead resting ECGs and exercise ("stress") ECGs"; Department of Biological Sciences: printed from website http://www.ndsu.edu/pubweb/rvgrier; printed on Jun. 7, 2010; 13 pages.
"Haberman et al., Wireless smart phone equipped ECG enables large scle screening in diverse populations. Unpublished abstract. 2 pages."
Hannaford, Kat; "How to Turn Your iPhone Into a Laser, Fan or Flashlight"; printed from website htto://m.qizmodo.com/5534904• printed on Feb. 3, 2011.
Hartmann, "ECG Front-End Design is Simplified with MicroConverter" AnalogDialogue, Nov. 2003, vol. 37, pp. 1-5.
Hayes, M.D.; "Approaches to Diagnosing Transient Arhythmias" An Overview; Mayo Clinic; Rochester Minnesota; (no date); pp. 7-10; printed on or before Apr. 14, 2010.
Hearing Loss Assoc. of Kentuckiana; Decibal Ratings/Hazardous Time Exposures of Common Noise (excerpt from Survivor's Manual); web version as of Oct. 5, 2008; 2 pgs.; printed Jun. 6, 2012 (http://web.archive.org/web/20081005143856/http://www.hearinglossky.orglhlasurvival1.html).
Hickey, et al. Detection of Recurrent Atrial Fibrillation Utilizing Novel Technology. Journal of Atrial Fibrillation. Dec. 2013-Jan. 2014; 6(4):50-52.
Huang, Tina; Age-related hearing loss; Minnesota Medicine; 90(10); pp. 48-50; Oct. 2007; printed Jun. 6, 2012 from: http://www.minnesotamedicine.com/PastIssues/PastIssues2007/0ctober2007/Ciinca1Huang0ctober2007.aspx).
IMEC News; IMEC extends flexible ECG patch to enable arrhythmia detection; printed from website http://www2.imec.be/imeC' printed on Aug. 18, 2009 1 page.
Instromedix. Cardiac Event Recording FAQ's; Instromedix A Card Guard Company, San Diego, CA.; printed from website www.instromedix.com/pdf/products/cardiac; printed on or before Apr. 14, 2010.
Instromedix. The Arrhythmia Monitoring System; King of Hearts Express AF Recorder Brochure from Instromedix• A CardGuard Company; Rosemont IL; 2004• 3 pages.
International search report and written opinion dated Feb. 24, 2014 for US Application No. PCT/US2013/069290.
Jenkins II, W.; Time/Frequency Relationships for an FFT-Based Acoustic Modem; Naval Postgraduate School; pp. 1-1 02; Sep. 2010 (http://edocs.nps.edu/npspubs/scholarly/theses/201 0/Sep/1 OSep_Jenkins.pdf) printed Oct. 2, 2013.
Kim, et al., "Detection of Atrial Fibrillation Episodes using Multiple Heart Rate Variabili!Y_Features in Different Time Periods", 2008, 4 pages.
Koerner. The Author's Metrics; Wired Magazine Article; New York, NY; Jul. 2009; p. 93-126.
Kumar, M.D., "Zio Patch", printed from website http://www.irhythmtech.com/zio-solution/zio-gach/, grinted on Apr. 12, 2010.

Kumparak, Greg; "Visa officially announces their case that turns your iPhone into a credit card (and we've got pies!)"; May 17, 2010; printed from website www.mobilecrunch.com• printed on Feb. 3, 2011.
Lau, et al. iPhone ECG application for community screening to detect silent atrial fibrillation: A novel technology to prevent stroke. Int J Cardiol. Apr. 30, 2013;165(1):193-4. doi: 10.1016/j.ijcard.2013.01.220. Epub Mar. 7, 2013.
Lau, et al. Performance of an Automated iPhone ECG Algorithm to Diagnose Atrial Fibrillation in a Community AF Screening Program (Search-AF). Heart, Lung and Circulation. 2013; 22:S205.
Lau et al. Validation of an iPhone ECG application suitable for community screening for silent atrial fibrillation—A novel way to prevent stroke (Presentation Abstract 16810); American Heart Association 2012 Scientific Sessions and Resuscitation Science Symposium; 126(1); Nov. 20, 2012.
Leijdekkers et al., "Trial Results of a Novel Cardiac Rhythm Management System using Smart Phones and wireless ECG Sensors", Proceedings of the th International Conf. on Smart homes and health Telematics., Jul. 1-3, 2009, Tours, France.
Levkov et al., "Removal of power-line interference from the ECG: a review of the subtraction procedure" BioMedical Engineering Online 2005, printed from website httg://www.biomedical-engineeringonline.com/contenU4/1/50 pp. 1-18.
Lowres et al., Feasibility and cost effectiveness of stroke prevention through community screening for atrial fibrillation using iPhone ECG in pharmacies. Thrombosis and Haemostasis, 111.6, 2014, 2 pages.
Lowres, et al. Screening Education and Recognition in Community pHarmacies of Atrial Fibrillation to prevent stroke in an ambulant population aged >=65 years (Search-AF stroke prevention study): a cross-sectional study protocol. BMJ Open. Jun. 25, 2012; 2(3); pii: e001355. doi: 10.1136/bmjopen-2012-001355.
M Med Choice; (company information page) Beijing Choice Electronic Technology Co., Ltd.; printed from website http://www.choicemmed.com/lxwm .asp; printed Dec. 28, 2009; 1 page.
M Med Choice. Handheld ECG Monitor Brochure; M Med Choice, Beijing Choice Electronic Technology Co. Ltd.• published on or before Apr. 14, 2010.
M Med Choice. Handheld ECG Monitor MD100A1; printed from website http://www.choicemmed.com/productshow.as_p; printed on Dec. 28, 2009; 2 pages.
M Med Choice. Handheld ECG Monitor MD100B; printed from website http://www.choicemmed.com/productshow.asp; printed on Dec. 28, 2009• 2 pages.
MacFarlane, et al. Resting 12-lead ECG electrode placement and associated problems; SCST update 1995; 15pgs. Printed Feb. 18, 2014 from www.scst.org.uk/resources/RESTING_12.pdf.
Mauvila: Mauvila ECG Tutorial; Basic ECG Interpretation Tutorial; Sections 1-12; 2004; printed from website http://mauvila.com/ECG/ecg.htm on Mar. 26, 2010; 57 pgs.
McManus et al., A novel application for the detection of an irregular pulse using an iPhone 4S in patients with atrial fibrillation. Heart Rhythm, 10:315-319 (2013).
MedGadget. Zio Patch Wins Medical Design Award MedGadget internet journal of emerging medical technologies, printed from website http://medaadaet.com/archives/2010/04/zio_patch_wins_medial_design_award_1.html.
MiCardioMobile: Remote Wireless Cardiac Rehabilitation Monitoring printed from website htto://alivetec.cable.nu/cardiomobile• printed on or before Apr. 14, 2010.
Mobility Mind. Use your Treo 650 as a portable ECG monitoring device, Mobility Mind Celebrating mobile Internet lifestyle and culture, Sep. 14, 2005, printed from website httg://www.treotoday.net/2005/09/14/use-your-treo-650-as-a-portab le-ecg-monitoring-device/.
Modem Protocols Explained; ftp://kermit.columbia.edu/kermit/cu/protocol.html; 5 pgs.; printed Oct. 2, 2013.
Modem Tutorial; http://www.lsu.edu/OCS/its/unix/tutoriai/ModemTutoriai/ModemTutorial.html; 2 pgs.; printed Oct. 2, 2013.
Muench, Frederick, PhD; "HRV: The Manurfacturers and Vendors Speak; The portable StressEraser Heart Rate Variability Biofeed-

(56) References Cited

OTHER PUBLICATIONS back Device: Background and Research". Biofeedback vol. 36 Issue 1, pp. 35-39• published Spring 2008.

Murph. RedEye mini converts iPhone, iPad or iPod touch into IR-beaming universal remote; printed from website http://www.engadget.com/2010/03/02/redeye; printed on Mar. 2, 2010; 3 pages.

Nam et al.; An Ultrasonic Sensor Based Low-Power Acoustic Modem for Underwater Communication in Underwater Wireless Sensor Networks; Computer Network Lab, Dept. of Elec. Eng., Korea Univ.; pp. 494-504; Dec. 2007 (http://nesl.ee.ucla.edu/fw/torres/home/Dropbox/good_paper_mico_controller.pdf; 11 pgs.; printed Oct. 2, 2013).

Neuroreille; Audiometry; web version as of Oct. 14, 2008; 1 pg.; printed Jun. 6, 2012 (http://www.neuroreille.com/promenade/english/audiometry/audiometry.htm).

Ochs. The Wello smartphone case puts health data in the palm of your hand. Mar. 6, 2014. TechHive blog. http://www.techhive.com/article/2105322/the-wello-smartphone-case-puts-health-data-in-the-palm-of-your-hand.html.

Omron; Omron Portable ECG EKG Handheld HCG-801 Monitor; printed from website http://www.amazon.com/Omron-Portable-Handheld-HCG-801-Monitor/dp/B0019WH3E0 on Feb. 24, 2010; 4 pgs.

Omron; Omron Portable ECG Monitor; printed from website http://www.target.com/gp/detail.html on Mar. 26, 2010; 1 pg.

Oresko, et al., "Detecting Cardiovascular Diseases via Real-Time Electrocardiogram Processing on a Smartphone", 2009 Workshop on Biomedicine in Computing: Systems, Architectures, and Circuits, pp. 13-16.

Perez, Sarah; No NFC? No Problem; New Startup Zoosh Provides Workaround Technology (Jun. 20, 2011 ); printed on or before Jun. 27, 2011 from website; 2 pgs.; (http://www.readwriteweb.com/archives).

Prystowsky, M.D.; "Chairmans Introduction"; Duke University Medical Center; Indianapolis, Indiana (no date)• pp. 5-6• printed on or before Apr. 14, 2010.

Prystowsky, M.D.; "Chairmans Summary"; Duke University Medical Center; Indianapolis Indiana; (no date); pp. 39-40• printed on or before Apr. 14, 2010.

Prystowsky, M.D., "The Clinical Application, Diagnostic Yield and Cost Considerations of Cardiac Event Recorders", Indianapolis, Indiana (no date) pp. 19-23. printed on or before Apr. 14, 2010.

Puurtinen, et al., Best Electrode Locations for a Small Bipolar ECG Device: Signal Strength Analysis of Clinical Data, Annals of Biomedical Engineering, vol. 37, No. s 2, Feb. 2009 (© 2008) pp. 331-336.

Raju Heart-Rate and EKG Monitor Using the MSP430FG439, SLAA280—Oct. 2005—Revised Sep. 2007, 11 pages.

Read-My-Heart. ECG Machine Handheld Read MyHeart; (product item No. HH-3413) printed from website http://www.helioliving.com/ECG-Machi ne-Handheld-ReadMyHea rt; printed on Feb. 4, 2010; 1 page.

Read-My-Heart; ReadMyHeart Personal Handheld ECG Monitor with Free Illustrator Book & Free Electrodes V2.2; printed from website http://www.amazon.com/Readmyheart-Personai-Handheld-illustrator-Electrodes/dp/B0010AN63W on Mar. 26, 2010; 1 pg.

Ricker. Square payment dongle demoed for iPhone toting hippies and you (video); printed from website http://www.engadget.com/2010/01/18/square-payment; printed on Jan. 18, 2010; 6 pages.

Rockwood. The Networked Body Magazine Article from Fast Talk Magazine; Jul./Aug. 2009; pp. 19-26.

Rohan. How to Save Lives with CE: Data Critical Corp's RhythmStat XLS Interview with developers David Albert, MD and Landgrave Smith, Ph.D. 1999. (http://www.bitcave.com/savelive.pdf).

Salahuddin, et al., "Ultra Short Term Analysis of Heart Rate Variability using Normal Sinus Rhythm and Atrial Fibrillation ECG Data", Engineering in Medicine and Biology Society, Aug. 2007, pp. 4656-4659.

Saxon, et al. Iphone rhythm strip—the implications of wireless and ubiquitous heart rate monitoring. J Am Coll Cardiol. 2012;59(13s1):E726-E726. doi:10.1016/S0735-1097(12)60727.

Saxon. Ubiquitous Wireless ECG Recording: A Powerful Tool Physicians Should Embrace. J Cardiovasc Electrophysiol. 24(4): pp. 480-483; Apr. 2013.

Semler, M.D.; "The Future of Cardiac Event Monitoring"; St. Vincent Hospital and Medical Center; Portland Oregon; (no date); pp. 33-37; printed on or before Apr. 14, 2010.

SFO Medical. Choice Portable Handheld ECG EKG Monitor; printed from website http://www.amazon.com/Choice-Portable-Handheld-ECG-Monitor/dp/B001Q74VOM; printed on Mar. 26, 2010; 1 page.

Shenzhen New Element Med. Equipment. Wireless ECG Monitoring System, printed from website http://www.alibaba.com/product-gs/248168581/Wireless_ECG_Monitoring_system.html., printed on Mar. 26, 2010.

Shumaker, J.; Designing an Ultrasonic Modem for Robotic Communications; Army Research Laboratory; 26 pgs.; Mar. 2009 (http://www.dtic.mil/cgi-bin/GetTRDoc?AD=ADA499556) printed Oct. 2, 2013.

Smith. Smartphone may keep the cardiologist away, The Independent, Health & Families, Mar. 5, 2010, printed from website http://www.independent.co.uk/life-style/health-and-families/healthnews/smartghone-may-keep-the-cardiologist-away-1916652.html, printed on Mar. 26, 2010.

Stevens, "Apple's Seamlessly Embedded Heart Rate Monitor could turn the iPhone into a new-age mood ring", printed from the website http://www.enaadaet.com on May 6, 2010, 3 pages.

Taleb Medical. Observer Hand-held ECG Monitor MD100B; (no date); printed on or before Apr. 14, 2010.

Tei, et al., New index of combined systolic and diastolic myocardial performance: a simple and reproducible measure of cardiac function—a study in normals and dilated cardiomyopathy; J Cardiol.; 26(6):357-366; Dec. 1995.

Telecompaper. Data Critical Launches Rhythmstat XL Medical System. Jan. 8, 1998. (http://www.telecompaper.com/news/data-critical-launches-rhythmstat-xl-medical-system--126725).

Texas Instruments. Information for Medical Applications, "Biophysical Monitoring—Electrocardiogram (ECG) Front End", Apr. 2004, 2 pages.

Tschida. Power A's New Case Turns Your iPhone Into a Universal Remote; printed from website http://appadvice.com/appnn; printed on Mar. 1, 2010• 2 pages.

U.S. Appl. No. 14/076,076 Office action dated Jan. 1, 2015.

U.S. Appl. No. 14/327,742 Office action dated Jul. 6, 2015.

Vanhemert, Kyle; "XWave Headset Lets You Control iPhone Apps With Your Brain"; Sep. 8, 2010; printed from website http://gizmodo.com; printed on Sep. 8, 2010.

Vitaphone. Telemedicine since 1999: Modern health management is our special subject. 3 pgs. Retrieved Mar. 19, 2014 from www.vitaphone.de/en/company/history-of-vitaphone/.

Wello by Azoi inc. 2014. https://azoi.com/.

Wikimedia Laboratories; Acoustics; web archive version dated Jan. 25, 2009; 2 pgs.; printed Jun. 6, 2012 (http://liveweb.archive.org/http://en.labs.wikimedia.org/wiki/Acoustics).

Wikipedia; Aliasing; web version as of Apr. 3, 2011; S pgs.; printed Jun. 6, 2012 (http://liveweb.archive.org/http://en.wikipedia.org/w/index.php?title=Aiiasing&oldid=422141882).

Wikipedia; Hearing Range; web version as of Feb. 6, 2010; S pgs.; printed Jun. 6, 2012 (http://web.archive.org/web/201 002062137 41/http://en.wikipedia.org/wiki/Hearing_range).

Wikipedia ."Pulse oximetry", printed from website httg://en.wikigedia.orq on May 10, 2010, 4 pages.

Wisneski, C.; Ultrasonic Local Area Communication; http://alumni.media.mit.edu/-wiz/ultracom.html; 2 pgs.; printed Oct. 2, 2013.

Woodward et al; "Bio-Potentiai-To-Frequency Converter/Modulator"; Electronic Design• Aug. 1999• p. 117.

Ziegler, Chris; "EPI Life phone sports ECG function, can let doctors know if you're gonna make it"; printed from website www.enoadoet.com/2010/06/; Jun. 17, 2010.

\* cited by examiner

DEVICES AND METHODS FOR REAL-TIME DENOISING OF ELECTROCARDIOGRAMS

CROSS-REFERENCE

This application is a continuation of U.S. application Ser. No. 14/327,742, filed Jul. 10, 2014, which claims the benefit of U.S. Provisional Application No. 61/844,850, filed Jul. 10, 2013, which applications are incorporated herein by reference.

BACKGROUND

The electrocardiogram (ECG) is widely used for diagnosis of heart diseases. Good quality ECGs are utilized by physicians for interpretation and identification of physiological and pathological phenomena. However, in real situations, ECG recordings are often corrupted by artifacts. Two dominant artifacts present in ECG recordings are high-frequency noise caused by electromyogram induced noise, power line interferences, or mechanical forces acting on the electrodes and baseline wander (BW) that may be due to respiration or the motion of the patients or the instruments. These artifacts severely limit the utility of recorded ECGs and thus need to be removed for better clinical evaluation.

Although methods have been developed for ECG enhancement, to date the real-time processing of ECGs has proven difficult, and yet critical to the success of ECG analysis. For example, many filtering techniques result in modifying the width and amplitudes of features in the ECG signal that are critical to interpreting the physiological implications of the signal. Described herein are ECG enhancement apparatuses (devices and systems) and methods configured to provide rapid and reliable de-noising of the ECG signal in real time.

SUMMARY

Described herein are apparatuses and methods configured to de-noise electrocardiogram (ECG) signals. In particular, described herein are methods for manually and/or automatically scaling the amount of de-noising applied to an ECG signal in real-time. Also described herein are methods and apparatuses adapted to combine multiple de-noising techniques to condition an ECG signal.

Aspects of the present disclosure provide a method of processing an electrocardiogram (ECG) signal of a user to provide improved readability of the ECG signal for a medical professional in diagnosing the ECG signal. An ECG signal may be received, for example, with a computing device. The ECG signal may be filtered as the ECG signal is received. The filtering may be performed by applying a first filtering stage, a second filtering stage, and a third filtering stage to the ECG signal. The first, second, and third filtering stages may be different from one another. The filtered ECG signal may be displayed in real-time as the ECG signal is received and filtered. The ECG signals may be displayed by a display of the computing device. The displayed filtered ECG signal can have improved readability such that a medical professional can more reliably diagnose the filtered ECG signal.

The first, second, and third filtering stages may be performed in sequence or in parallel. The first filtering stage may comprise removing baseline wander of the ECG signal, such as by removing a moving average of the ECG signal from a portion of the ECG signal. The second filtering stage may comprise removing high-frequency noise from the ECG signal, such as by applying a Savitzky-Golay de-noising filter to smooth the ECG signal. This Savitzky-Golay de-noising filter may be applied by applying a high order Savitzky-Golay filter to a QRS segment of the ECG signal and applying a low order Savitzky-Golay filter to a non-QRS segment of the ECG signal. The third filtering stage may comprise removing low-amplitude, high frequency noise from the ECG signal, such as by applying threshold fit smoothing to the ECG signal.

The received ECG signal may be pre-processed before filtering the ECG signal such as by applying user-selected mains filter.

Furthermore, an amount of noise of the received ECG signal may be detected. An amount of filtering applied to the received ECG signal may be varied in response to the amount of noise detected. To detect the amount of noise, a module of the computing device may be trained with a noise model. Alternatively or in combination, the amount of filtering applied to the received ECG signal may be varied in response to user input.

Aspects of the present disclosure also provide a method of processing an electrocardiogram (ECG) signal of a user to provide improved readability of the ECG signal for a medical professional in diagnosing the ECG signal. An ECG signal may be provided to a computing device. The ECG signal may be filtered and displayed such as on a display of the computing device. An amount of filtering applied to the displayed ECG signal may be varied in response to user input. The amount of filtering may be varied in real-time as the ECG signal is displayed. The displayed filtered ECG signal may have improved readability such that a medical professional can better diagnose the filtered ECG signals.

To provide the ECG signal, the computing device may receive the ECG signal as the ECG signal is measured from an ECG sensor coupled to the computing device. Alternatively or in combination, the computing device may receive the ECG signal as the ECG signal is measured from an onboard sensor of the computing device.

Generally, the ECG signal is displayed in real-time as the ECG signal is provided and filtered. To filter the displayed ECG signal, a first filtering stage, a second filtering stage, and a third filtering stage may be applied to the received ECG signal, wherein the first, second, and third filtering stage are different from one another.

The computing device may comprise one or more of a smartphone, a tablet computer, a laptop computer, a personal computer, a personal digital assistant, or a wearable computer.

Aspects of the present disclosure also provide a method of processing an electrocardiogram (ECG) signal of a user. The ECG signal may be received, pre-processed, and then filtered by (i) removing baseline wander of the ECG signal, (ii) removing high frequency noise from the ECG signal, and (iii) removing low-amplitude, high frequency noise from the ECG signal, wherein steps (i) to (iii) are performed sequentially.

Aspects of the present disclosure also provide a computer readable medium comprising a set of instructions that when executed by a processor cause the processor to receive an ECG, filter the received ECG signal in-real time with a multi-stage filter, and cause the filtered signal to be displayed on a display in communication with the processor. The set of instructions when executed by the processor may also cause the ECG signals, filtered or unfiltered, to be stored on a memory in communication with the processor or to be transmitted to a remote computing device such as a remote server for storage and/or analysis either automatically or through a medical professionals. The set of instructions when executed by the processor may cause the processor or circuitry in communication with the processor to execute any of the methods, steps, or sub-steps described herein. The set of instructions may be provided on a memory of the computing device which may comprise any of the computing devices described herein. The processor may comprise a processor or other circuitry of the computing device.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the invention are utilized, and the accompanying drawings of which:

DETAILED DESCRIPTION

Figure 1:
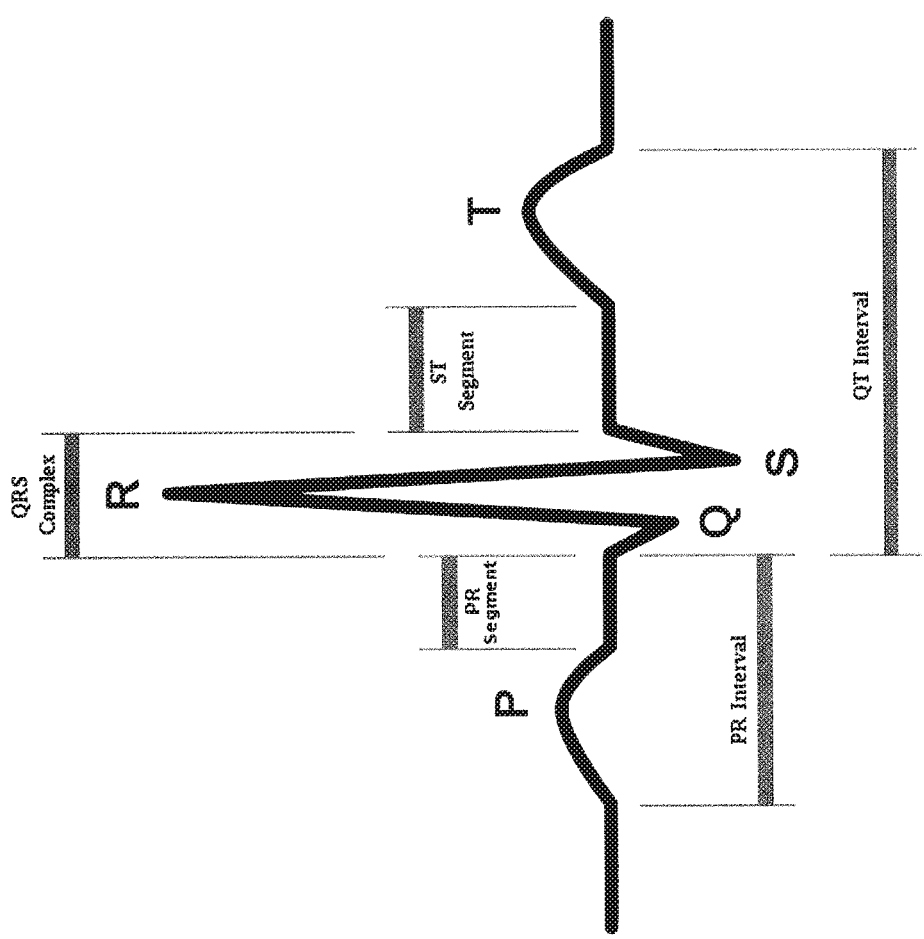
FIG. 1 illustrates an ideal version of an ECG signal, showing the PQRST components of the ECG trace.

In general, an apparatus may include multiple filtering modules for de-noising an ECG signal. In particular, de-noising modules may be configured to operate in real-time. The apparatus may be configured to receive (or record) an ECG signal; the ECG signal may be digital or converted to a digital signal. The ECG signal may be analyzed to determine wherein the signal (or which portion of the signal) is likely to include a QRS portion of the signal. As illustrated in FIG. 1, a typical ECG signal includes a QRS complex having a rapid rise (peak) that may be readily determined. The peak location of the QRS complex in a signal may be determined based, for example, of the presence of a "spike" in the signal, particularly a spike having a characteristic rise and/or fall time.

Described herein are methods and apparatuses implementing these methods, for applying multiple de-noising techniques to a real-time ECG signal (e.g., from a moving window of an ECG as it is received by a device) enhancing the display of the ECG signal. Thus, this may be described as a visual de-noising or visual filtering. Multiple de-noising filters may be combined either in parallel or sequentially or both to provide a final de-noised output. In addition, the "percentage" of filtering applied may be manually or automatically selected. This percentage of filtering may be applied either to the overall de-noising, or to some or all of the different de-noising techniques (modules) included. For example, a raw digital ECG signal may be 100% de-noised by the filtering system, or it may be filtered some lesser percentage (e.g., 90%, 80%, 70%, etc.). In some variations, the amount (by percent) of each (or some) of the de-noising techniques may be selected (e.g., 100% baseline wander correction, 50% Savitzky-Golay de-noising, 50% threshold smoothing, etc.).

Also described herein are methods of de-noising using feedback based on the quality of the ECG signal received. For example, an apparatus may apply more filtering/de-noising when the raw ECG is noisier (has a higher signal-to-noise ratio), and less filtering/de-noising when the signal is less noisy, to prevent loss of signal information.

In the example below, three types of de-noising are described: baseline wander correction, Savitzky-Golay de-noising, and Threshold smoothing, and one variation of a method for applying these three de-noising techniques is illustrated. It should be understood that other techniques for de-noising, including other de-noising techniques ("modules") and way to combine them are possible and encompassed by the inventions described herein.

EXAMPLE 1

Real-Time Visual Filtering

Figure 2:
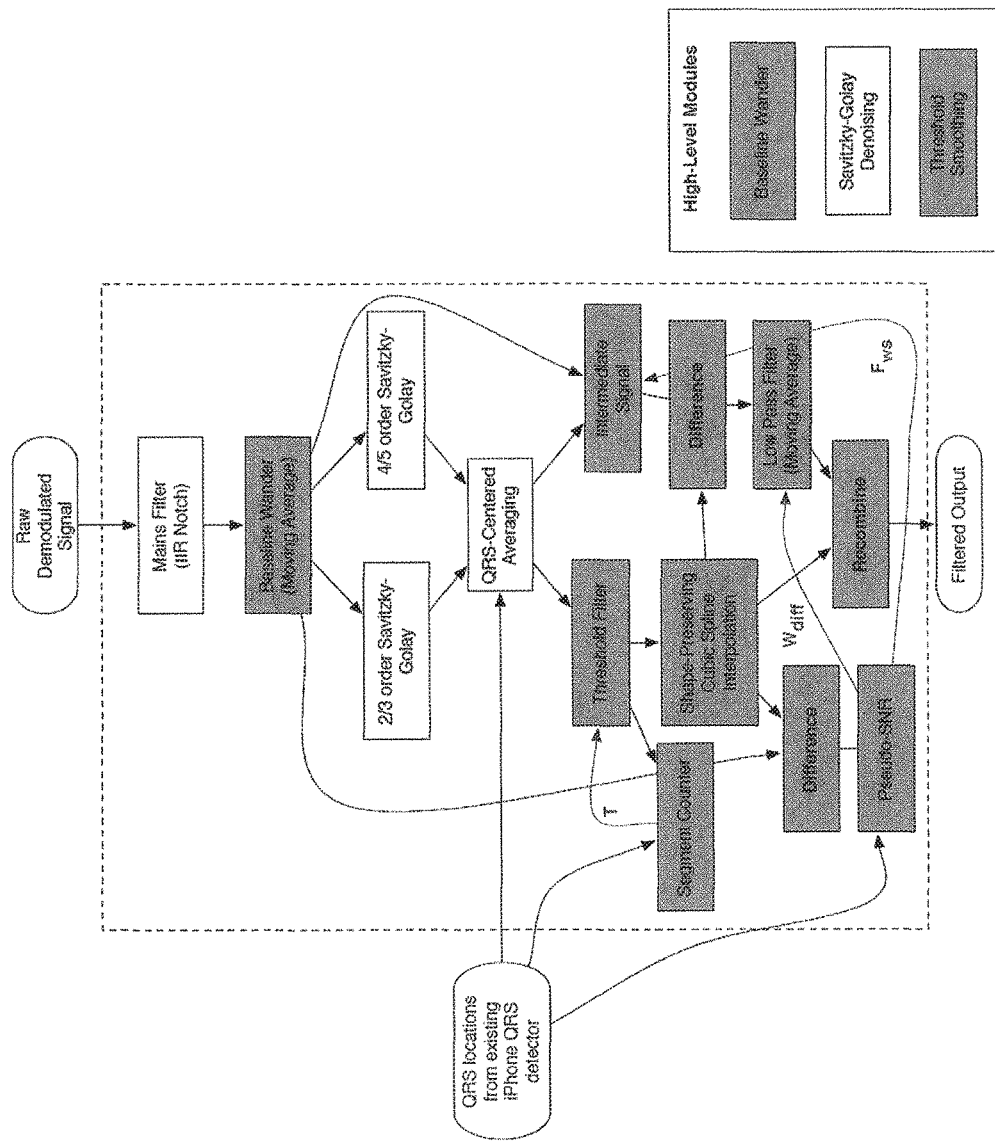
FIG. 2 is a flow diagram showing an overview of one variation of a method for de-noising an ECG signal.

In one example, a real-time visual filter is composed of three high-level stages which operate on the signal approximately in order: baseline wander removal, Savitzky-Golay de-noising, and threshold-fit smoothing. FIG. 2 illustrates one variation, showing an overview of the operation of these three techniques. In FIG. 2, as in any of the variations discussed herein, the raw (demodulated) signal may first be pre-processed to remove mains noise. For example, as a pre-processing step before the main processing stages, an apparatus may apply an IIR notch filter at the mains frequency to remove mains noise.

In one example, the mains filter is a 2nd-order IIR notch filter with a stop-band centered at a user-selected (or preselected) mains frequency (e.g., 50 KHz, 60 KHz, etc.). The mains filter may operate directly on the raw data received from the FM demodulator (or other digital ECG signal source).

In any of the variations described herein, each de-noising module may be referred to as a stage, and in some variations, each stage operates independently of the other stages, and is not tightly coupled to the other stages. This may allow each stage to be modified, improved, or replaced without substantially affecting the behavior of subsequent stages.

In the example shown in FIG. 2, and described below, the real-time visual de-noising apparatus dynamically adjusts certain filter parameters based on the estimated quality and noise characteristics of the input signal.

Baseline Wander

Any appropriate baseline wander filter that provides real-time adjustment of the baseline (e.g., to restore it to zero) may be used. In one variation, the baseline wander removal stage is a centered moving-average filter, with a fixed window size, $W_{avg}$. This stage removes baseline wander by subtracting from each sample the average of the previous $W_{avg}/2$ and next $W_{avg}/2$ samples. For example, when $W_{avg}$=401 samples, the window size will be longer than the R-R interval for heart rates of 45 bpm or greater (for many appropriate sample rates).

Further, in some variations, in calculating the moving average the 40 samples surrounding each detected QRS (+/−20 samples from the detected QRS location) may be excluded. Thus, the baseline wander module may receive information about the location (e.g., estimated midpoint) of a QRS location.

In some variations, the baseline wander module may include a parameter such as window size ($W_{avg}$) for the number of samples. This parameter may be set/fixed or adjusted either manually or automatically.

Savitzky-Golay De-noising

The purpose of the Savitzky-Golay de-noising stage is to remove high-frequency noise from the signal without compromising the shape or relative amplitude of the morphological components. Savitzky-Golay filters are a class of FIR filters that essentially perform a local polynomial fit to the data in the signal. When the parameters of the filter are chosen properly, a Savitzky-Golay filter can remove noise while preserving the width and amplitude of features in the signal.

However, the order and window size of the filter must be chosen properly relative to the features that are intended to be preserved. One example of an implementation of this stage uses two Savitzky-Golay filters, a high-order filter used around the QRS complexes, and a low-order filter used everywhere else in the signal. As suggested by FIG. 2, a QRS detector (e.g., in the apparatus or system used to acquire the ECG signal or in the pre-processing of the window of ECG data) may be used to locate QRS complexes in the signal, and the output of the two filters may be combined using a weighted moving average. The high-order mixing weight ($w_{mixing}$) may be set to zero everywhere except for a Gaussian centered on each QRS location with peak amplitude 1 and a FWCM (full-width at $\frac{1}{100}$th max) $G_{mixing}$. The final output signal is then generated from the weight $w_{mixing}$ and the two Savitzky-Golay filter outputs $S_{high}$ and $S_{low}$ according to a weighting technique, such as that illustrated in the following formula:

$$\text{Out}=S_{low}*(1-w_{mixing})+S_{high}*w_{mixing}$$

In some variations, the module including the one or more Savitzky-Golay de-noising/filtering may include one or more parameters that can be fixed or modified either manually and/or automatically. For example, Parameters that may be adjusted include: High-order filter order (e.g., $4/5$), High-order filter window (samples) (e.g., 15), Low-order filter order (e.g., $2/3$), Low-order filter window (samples) (e.g., 15), and QRS Mixing Width $G_{mixing}$ (samples) (e.g., 60).

Threshold-Fit Smoothing

A threshold-fit smoothing (TFS) stage may perform additional smoothing of the signal to remove any low-amplitude, high-frequency noise remaining after the Savitzky-Golay denoising. The parameters used in the TFS stage may be dynamically adjusted based on the estimated noise content of the signal. The basic operation of the TFS stage will be discussed first, and then the adaptation mechanism.

The TFS stage first transforms the signal into a set of horizontal and vertical segments. The algorithm processes the signal in order. Starting with the beginning of the signal, or the end of the last segment generated, the algorithm generates a new horizontal segment whenever the signal range (the difference between the maximum and minimum signal value over the segment domain) exceeds a specified absolute threshold T. At this point, a new horizontal segment is generated with an amplitude corresponding to the average value of the signal over the segment domain, and a vertical segment is generated connecting the previous horizontal segment to this new horizontal segment.

Examples parameters of the threshold-fit smoothing/filter that may be fixed or adjustable (including automatically adjustable by the adaptation mechanism described below) include: Segment Threshold T (mV), which may be variable/adjustable and have a default=0.05; Difference Window $W_{diff}$ (samples) which may be variable/adjustable and have a default=21; Maximum Segment Length $M_p$ (samples) (e.g., 80); and Intermediate Signal Mixing Fraction $F_{ws}$, which may be variable/adjustable and have a default=1.0.

Subsequently, the midpoints of each segment (both the horizontal segments and vertical segments) may be computed, and a shape-preserving cubic fit interpolation may be used to generate a smooth function $S_{tf}$ connecting these points.

An intermediate signal $S_I$ may be generated from a weighted average of the output of the baseline wander filter $S_w$, and the output of the Savitzky-Golay filter $S_{SG}$. The weight may be given, in one variation, by the intermediate signal mixing fraction $F_{ws}$, such that $S_I=F_{ws}*S_{SG}+(1-F_{ws})*S_w$.

The interpolated/smoothed function $S_{tf}$ may be subtracted from the intermediate signal $S_I$. The difference may then filtered by a centered moving average filter with window size $W_{diff}$, and this filtered difference may then added back to the smoothed function $S_{tf}$ to produce the final output of the stage.

Because the filtering may be performed in real time and because this may require a certain minimum number of points to perform the cubic fit interpolation, the algorithm may impose a maximum segment length. For example, the algorithm may require that there be at least 3 segments in every $M_p$-sample interval.

Adaptation

As mentioned, the apparatus may automatically adjust the amount of filtering (and type of filtering/de-noising) based on the need or demand, as determined from the quality of the signal. For example, optimal values for the TFS parameters may depend on the noise characteristics of the signal. Is it known that parameters that lead to good noise reduction on noisy signals can produce over-filtering of clean signals. We developed an adaptation mechanism that produces an estimate of the noise characteristics of the signal and adjusts the TFS parameters accordingly. This automatic or "adaptation" mechanism may use two or more independent measures.

For example, first the apparatus may count the number of horizontal segments generated by the TFS filter between each pair of QRSs. Segments with length 1 (i.e. segments generated when the signal changes by more than the current threshold T between samples, such as in a QRS) are excluded. After the sample corresponding to the detected location of each QRS is output from the filter, the threshold T is adjusted based on the number of segments in the last QRS-to-QRS interval, so as to try to keep the number of length >1 segments in those intervals at approximately 30.

Second, from each QRS, the apparatus may compute a "pseudo-SNR" associated with that QRS by subtracting the output of the interpolated/smoothed signal $S_{tf}$ from the output of the baseline wander filter SW to produce a "pseudo-noise" signal SSN. Then, for a window centered on the detected QRS location extending +/−150 samples forward and backward, but excluding the innermost +/−20 samples around the QRS, the algorithm calculates the pseudo-SNR by dividing the standard deviation of the pseudo-noise signal by the standard deviation of the smoothed signal $S_{tf}$ (note that this is technically a "noise-to-signal ratio," i.e. it is larger when more noise is present). This pseudo-SNR is then multiplied by 100.

The average of the pseudo-SNR associated with the last 5 QRSs is stored as the "recent pseudo-SNR" ($R_{snr}$). This parameter may then be used to update the difference window $W_{diff}$ parameter and intermediate signal mixing fraction $F_{ws}$, for example, according to a relationship such as:

$$W_{diff} = \text{round}\left(\frac{\min(21, R_{snr})}{2}\right)$$

$$F_{ws} = \min\left(1, \frac{R_{snr}}{20}\right)$$

The purpose of the first mechanism is to keep the threshold value T properly scaled relative to the amplitude of the received ECG signal. The purpose of the second mechanism is to gradually reduce the amount of filtering that is applied based on the estimated amount of noise present in the signal, such that cleaner signals are subjected to less-aggressive filtering (note that, in the extreme of 0 noise, with $W_{diff}=1$ and $F_{ws}=0$, the TFS stage would simply output the unaltered baseline wander signal $S_{ws}$ bypassing the Savitzky-Golay filtering as well as the threshold/fit smoothing).

Comments on Implementation

The described filter configuration illustrated in FIG. 2, above, represents just one possible instance of a broad class of filters (filter configurations) that can be implemented using the threshold segment extraction (fit smoothing) recombination approach illustrated in this example. All numerical values provided as examples above, such as the window size used for calculating the pseudo-SNR, target number of segments, as well as the adaptive parameter relationships were chosen empirically and good or perhaps better behavior could conceivably be obtained with different choices for these parameters.

Shape-preserving cubic fit implementations appropriate for use as described herein have been previously described, although not in the context of the apparatus and methods described herein. For example, see F. N. Fritsch and R. E. Carlson, Monotone Piecewise Cubic Interpolation, *SIAM Journal on Numerical Analysis,* 17 (1980), pp. 238-246, and the default MATLAB implementation of it (as "pchip.m,"). Compared to an ordinary cubic fit interpolation, the "shape-preserving" fit sets the local slope of the interpolation points to prevent the interpolated signal from over or undershooting the local sample values. This produces a smooth, visually-pleasing interpolation that connects the sampled points without introducing spurious ringing or oscillation, e.g. frequency components not present in the sampled data. A comparison of this interpolation with a standard cubic fit interpolation is shown below (taken from MATLAB documentation on pchip.m).

Figures 3A, 3B:
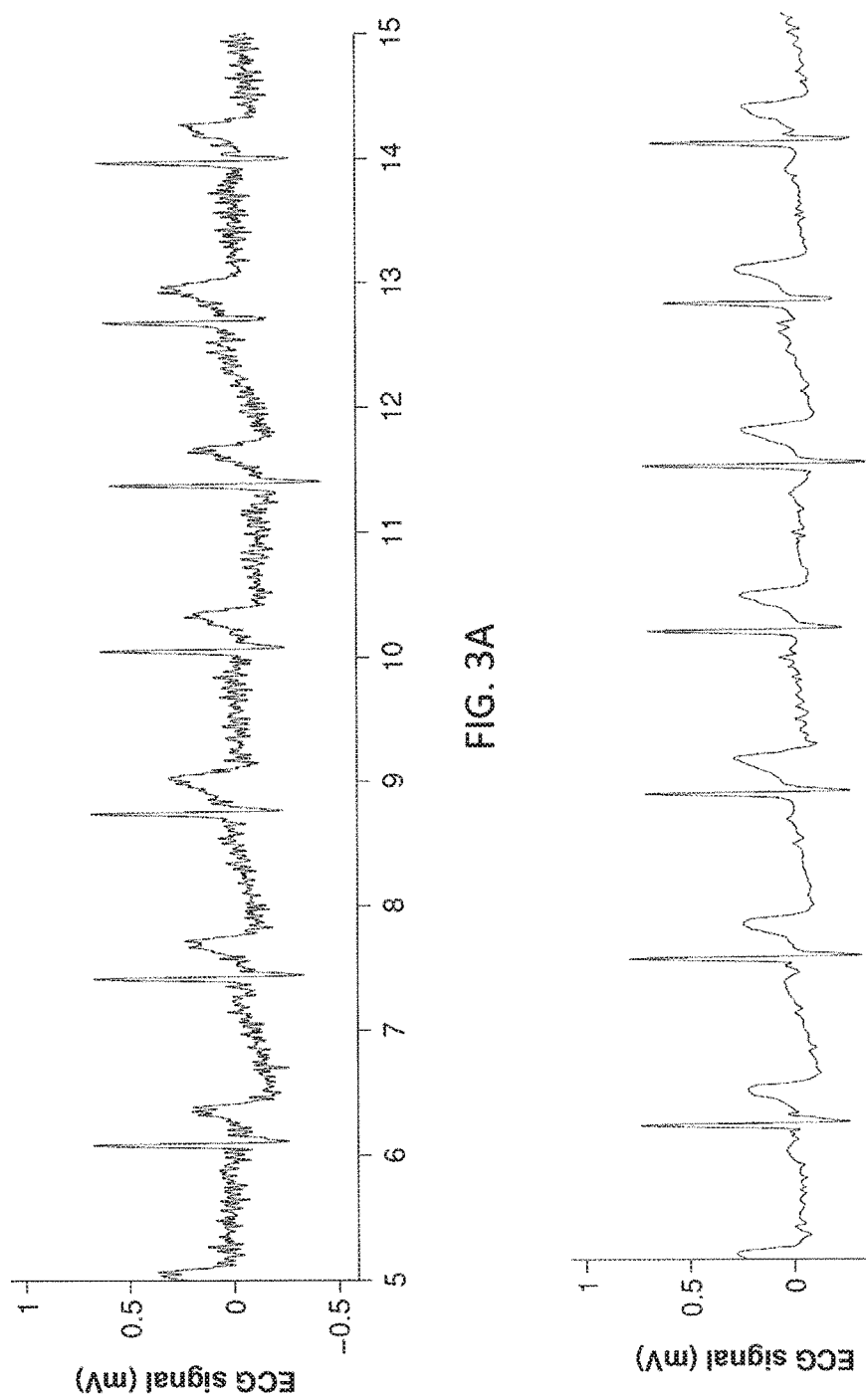
FIG. 3A shows one example of an ECG trace before applying any filtering.
FIG. 3B shows the same trace, with 100% of the filtering (applied). The de-noising technique used includes the use of a module for each of baseline wander correction, Savitzky-Golay de-noising, and threshold smoothing, similar to that illustrated in FIG. 2.

FIG. 3 (as well as FIGS. 5 to 7) illustrate the operation of a de-noising technique employing the three modules illustrated above. In this example, FIG. 3A shows an example of an ECG recording both without (FIG. 3A, showing the raw ECG signal) and with (FIG. 3B) the real-time de-noising using a baseline wander correction technique, a pair of Savitzky-Golay de-noising filters and threshold smoothing.

As can be seen in FIG. 3B, the high-frequency noise has been mostly eliminated, revealing an ECG signal (including multiple QRS peaks) that may provide significant clinical information.

In FIGS. 3A and 3B the raw and de-noised signals are compared. Also described herein are systems and methods allowing manual (or automatic) control of the overall amount (percent) of de-noising applied. In this context, for example, FIG. 3A shows 0% (no) de-noising applied, while FIG. 3B shows 100% de-noising applied to the signal.

Figure 4:
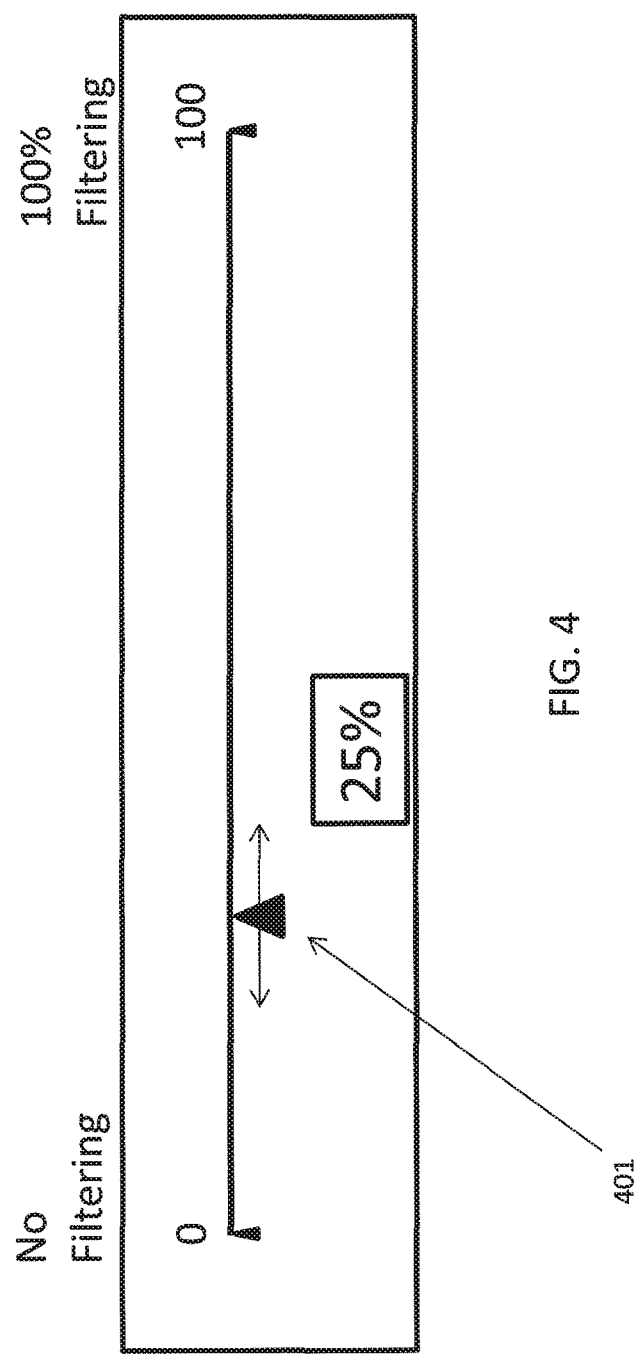
FIG. 4 schematically illustrates a manual selector for selecting the percent of filtering to be applied.
Figure 5A:
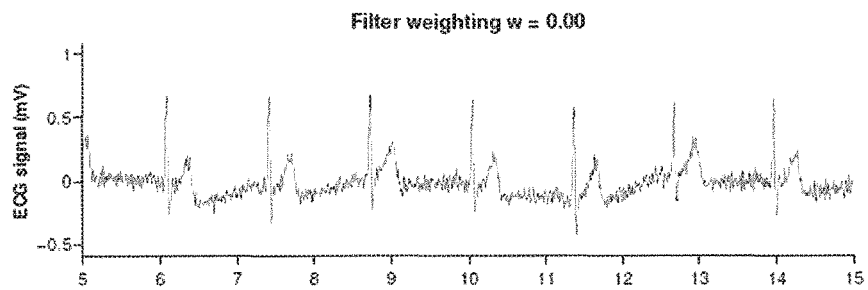
FIGS. 5A-5E illustrate an ECG trace with increasing amounts of filtering (de-noising) manually selected.
Figure 5B:
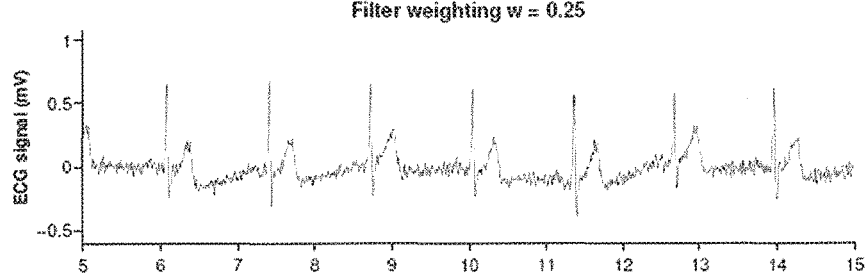
Figure 5C:
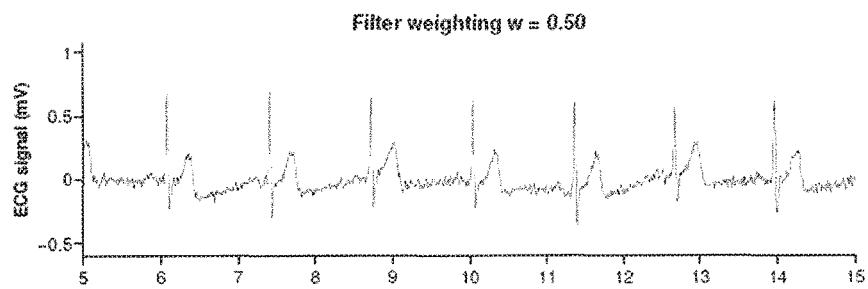
Figure 5D:
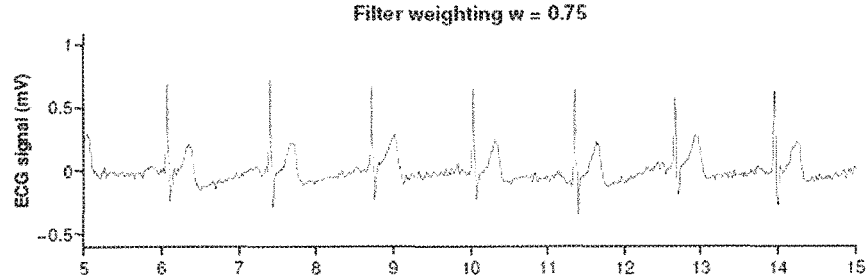
Figure 5E:
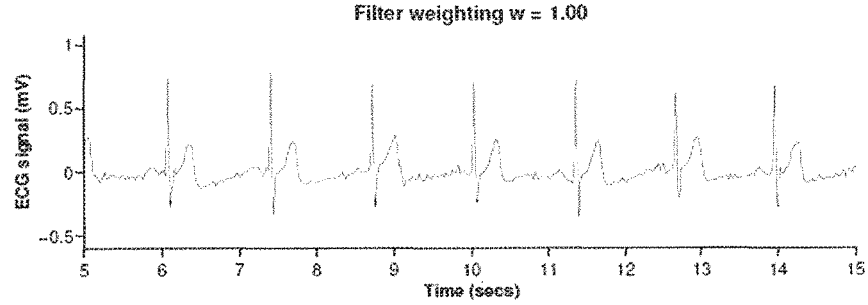
Figure 6A:
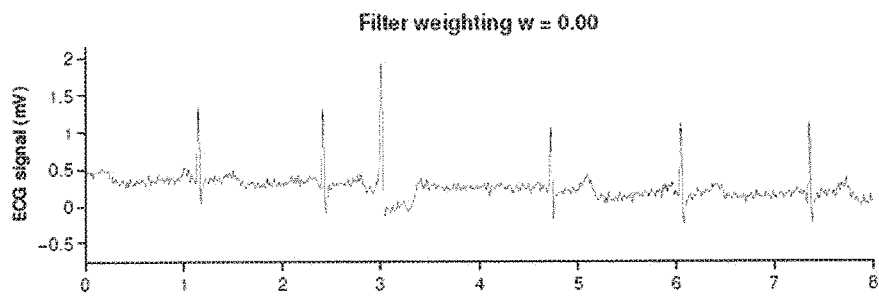
FIGS. 6A-6E illustrate an ECG trace with increasing amounts of filtering (de-noising) manually selected.
Figure 6B:
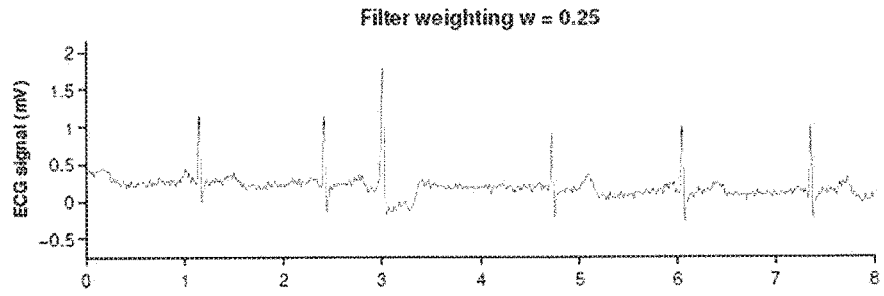
Figure 6C:
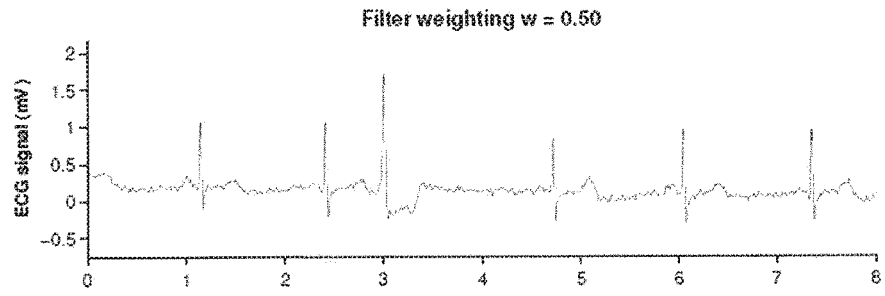
Figure 6D:
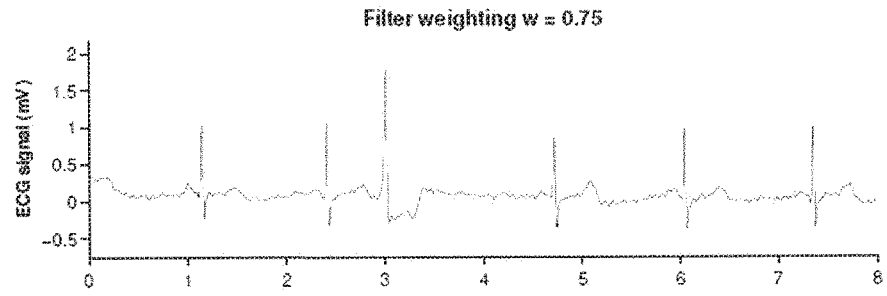
Figure 6E:
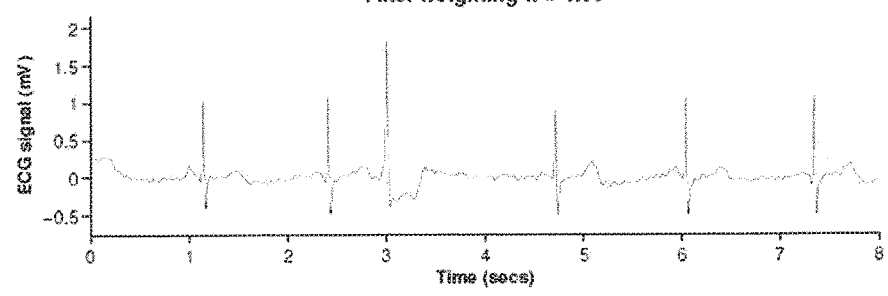
Figure 7A:
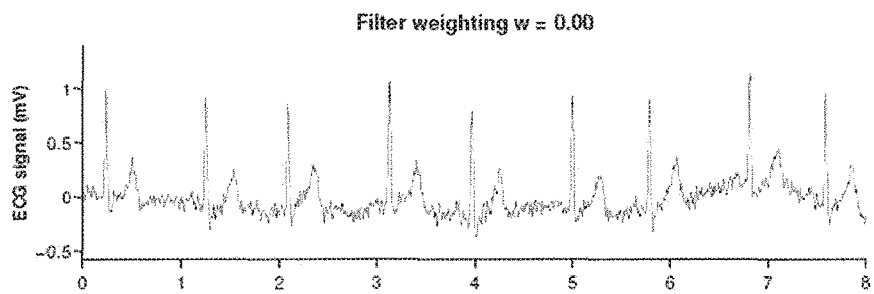
FIGS. 7A-7E illustrate an ECG trace with increasing amounts of filtering (de-noising) manually selected.
Figure 7B:
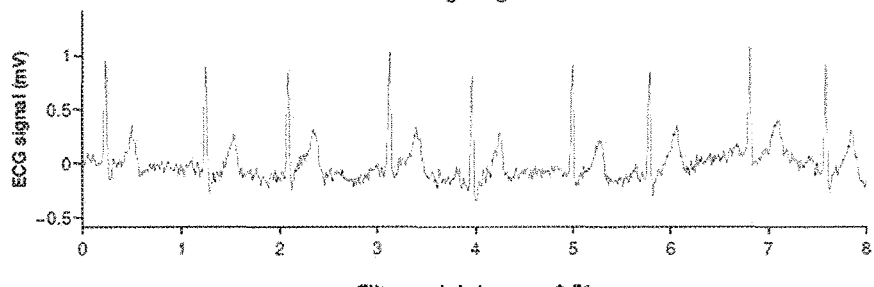
Figure 7C:
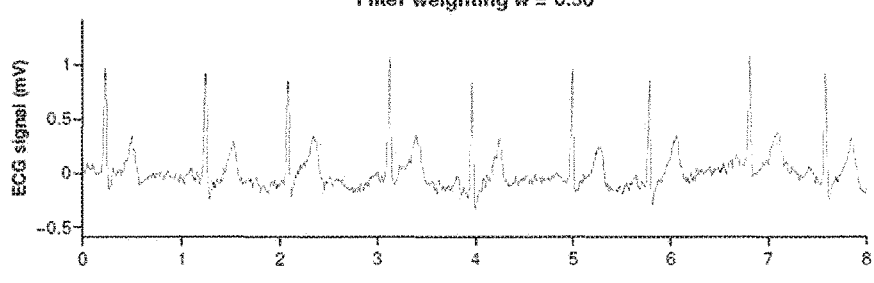
Figure 7D:
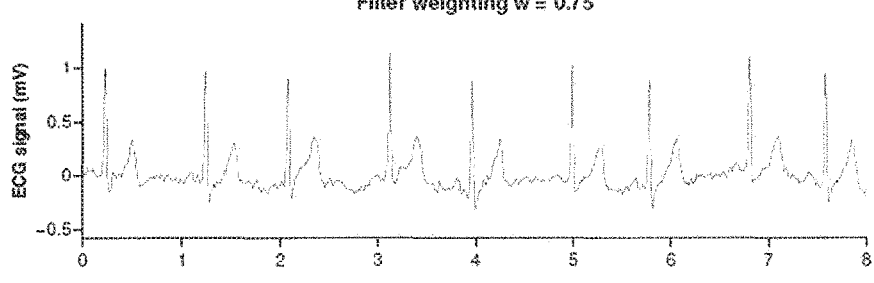
Figure 7E:
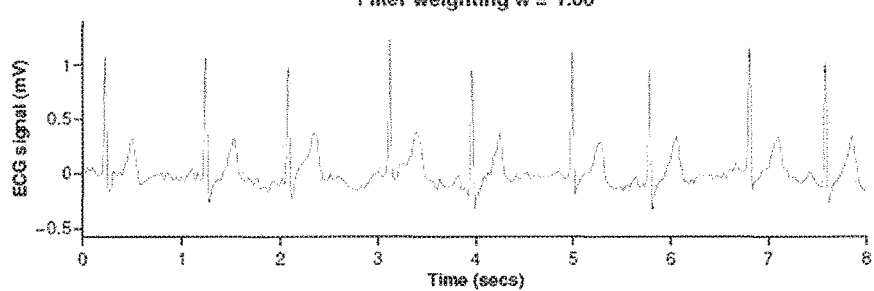

For example, FIG. 4 shows a representation of a manual selector 401 (e.g., slider, switch, input), for selecting how much de-noising to apply. In some variations, this applies to any and all filtering/de-noising; in some variations this module may be configured to select the percent of de-noising excluding the preprocessing (e.g., main filter) and/or the baseline wander correction. For example, the apparatus or method may be configured to allow manual selection of the high-frequency filtering (e.g., Savitzky-Golay denoising and/or threshold smoothing).

In FIG. 4, the slider is set to 25%, but may be adjusted between 0 and 100 percent (e.g., 0 and 1). This may be achieved by weighting the amount of filtering applied. For example, the output (visual output of the ECG) may be weighted by the filtering based on the following relationship:

The output at time t is:

$$\text{Output at time } t = (1-w)*A(t)+w*B(t)$$

Where w is the percent of weighting for the de-noising (e.g., the slider setting in FIG. 4), and A(t) is the raw or low-filtered signal, and B(t) is the filtered/de-noised signal. In this example, the A(t) and B(t) signals are time aligned, as this is being performed in real-time.

In use, a physician or use may look at an ECG signal and, on the screen, move the percent de-noising selector (e.g., slider) to select how much de-noising to show. If there is an unusual shape in an ECG signal, they can confirm that it is a genuine effect, and can gradually move the selector to confirm that the feature is genuinely present, and how it is affected by the de-noising.

In some variations, an apparatus (system or device) may be configured to remove mains noise and do low-pass filtering when the percent de-noising is set to zero. However, the apparatus could be configured to more filtering to show the raw signal (without preprocessing or baseline wander correction), as mentioned.

FIGS. 5A-5E, 6A-6E and 7A-7E illustrate three ECG traces showing various amounts of filtering/de-noising applied. FIGS. 5, 6 and 7 all show 'raw' signals prior to filtering, and FIGS. 5E, 6E and 7 (respectively) show the same signals with 100% of the de-noising applied.

As discussed above, the apparatus or method may also be configured to automatically/adaptively adjust the amount of de-nosing provided. For example, the system may be configured to weight the application of de-noising more or less based on a detected noise level for the signal. Thus, the quality of the signal may determine the amount of filtering to be applied. In some variations, automatic detection of noise could be done by training a non-linear regression model (e.g., a neural network) on signals that are clean (e.g., 1000 clean ECG signals), from which a noise model can be built. By adding on different degrees of noise, and make a noisy signal, the system/module may be trained to learn to detect relative percentage of noise. This may let one determine how much noise is present (by approximate) and determine the amount of filtering to apply.

EXAMPLE(S)

Figure 8:
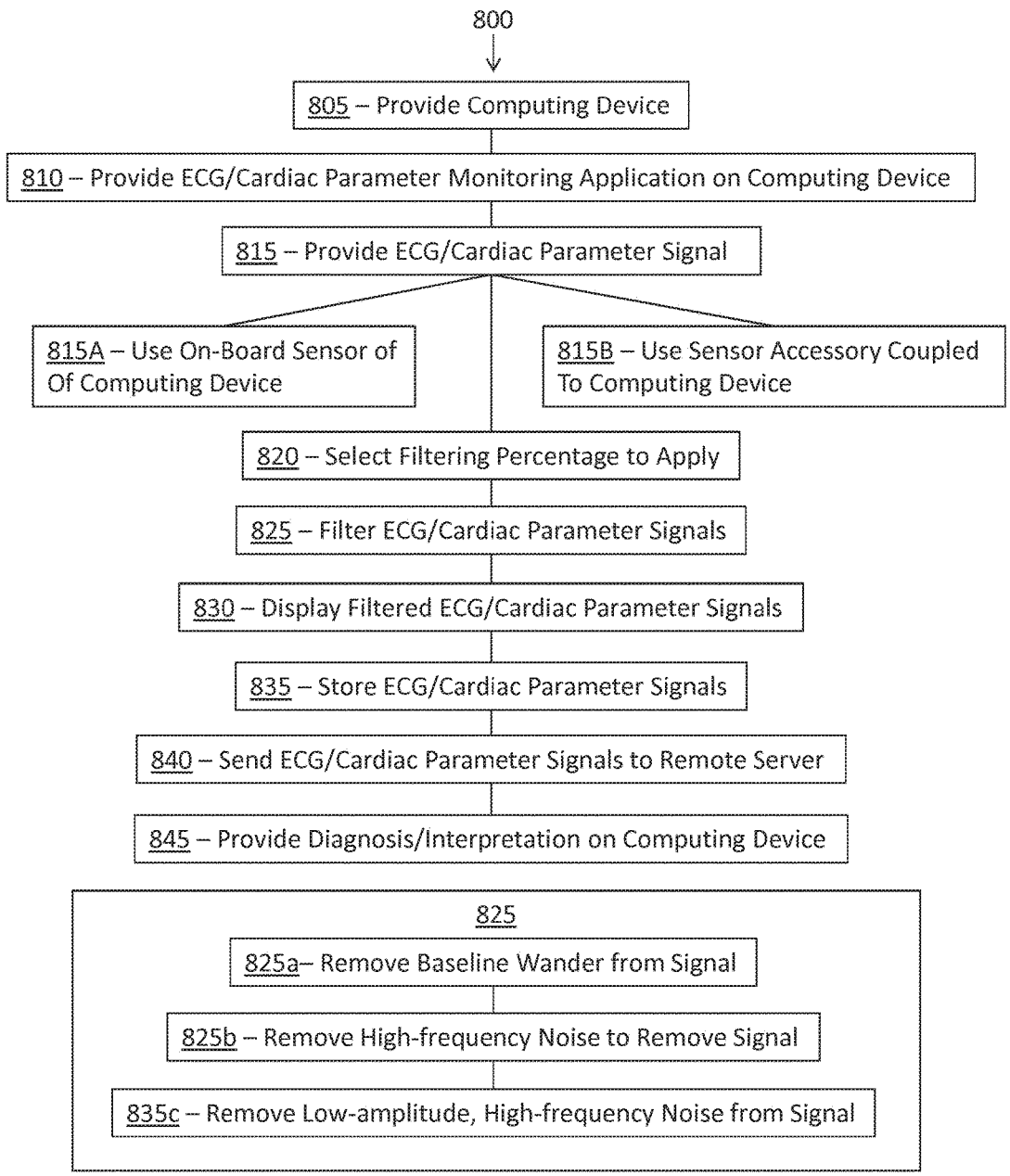
FIG. 8 shows a flow chart of an exemplary method of monitoring an ECG signal in accordance with many embodiments.

The ECG filtering methods and apparatuses described herein can be used for many ECG signals acquired from many sources. For example, the ECG signals may be conveniently acquired through the use of an everyday computing device such as a personal computer, a laptop computer, a tablet computer, a smartphone, a smart watch, a smart wrist band, a wearable computer, or the like. FIG. 8 shows an exemplary method 800 of monitoring an ECG signal of a user through the use of such computing devices.

In a step 805, the computing device may be provided. The computing device may comprise an everyday use computing device as described herein. In a step 810, an ECG or cardiac parameter monitoring application may be provided on the computing device. For example, the ECG or cardiac parameter monitoring application may be downloaded from an application distribution platform such as the Apple iTunes or App Store, Google Play, Amazon App Store, or the like. The application may be loaded and active on the computing device to monitor the ECG or cardiac parameter(s). Alternatively or in combination, the application may be placed in the background and remain active to monitor the ECG or cardiac parameter(s) while a second application such as a Web Browser or e-mail client is active.

In a step 815, the ECG or cardiac parameter signal may be provided. The ECG or cardiac parameter signal may be provided from an on-board sensor assembly of the computing device. For example, an on-board sensor of the computing device may be used in a step 815A. The computing device may comprise a plurality of built-in electrodes to measure an ECG of a user upon contact with the skin of the user (e.g., such as on the chest or on two or more limbs). The ECG or cardiac parameter may be provided from an accessory in communication with the computing device. Alternatively or in combination, a sensor accessory coupled to the computing device may be used in a step 815B. The accessory may comprise a plurality of electrodes to measure an ECG of the user upon contact with the skin of the user (e.g., such as on the chest or on two or more limbs) and a wireless transmitter for wirelessly transmitting the measured ECG signal to the computing device. The accessory may be in the form of a computing device cover or case or a wristlet. Such accessories are described in co-assigned U.S. patent application Ser. No. 12/796,188 (now U.S. Pat. No. 8,509,882), Ser. Nos. 13/108,738, 13/420,520 (now U.S. Pat. No. 8,301, 232), Ser. Nos. 13/964,490, 14/254,310, 61/845,254, 61/872,555, 61/874,806, and 61/982,002.

In a step 820, an amount of filtering may be selected to be applied to the ECG or cardiac parameter signal. Such selection may be as described above. For example, the application may have a menu bar which may be dragged by the user to select a percentage of filtering to apply (e.g., the menu bar may be provided on a touch-screen display). In a step 825, the selected filter is applied to the ECG or cardiac parameter signal. The applied filter may comprise the multistage filter described above. For example, the step 825 may comprise three or more distinct filtering steps 825a, 825b, and 825c. In a step 825a, a baseline wander of the signal may be removed such as by removing a moving average of the signal from a portion of the signal as described herein. In a step 825b, high-frequency noise may be removed to smooth the signal such as by applying a Savitzky-Golay de-noising filter as described herein. In a step 825c, low-amplitude, high-frequency noise is removed from the signal such as by applying threshold fit smoothing as described herein. In a step 830, the filtered ECG or cardiac parameter signal is displayed, for example, with a display of the computing device.

The ECG or cardiac parameter signal, filtered or unfiltered, may be analyzed either automatically by the application loaded onto the computing device or by a medical professional, either observing the signal shown by the display of the computing device or observing the signal remotely. In a step 835, the ECG or cardiac parameter signal may be stored on a memory of the computing device. In a step 840, the ECG or cardiac parameter may be sent to a remote server, for example, wirelessly through the Internet. The ECG or cardiac parameter may be remotely analyzed in many ways. For example, the ECG or cardiac parameter may be analyzed using a plurality of medical professionals as described in co-assigned U.S. patent application Ser. No. 14/217,032. In a step 845, a diagnosis or interpretation of the ECG or cardiac parameter can be provided on the computing device. For example, a medical professional remote server can upload the diagnosis or interpretation to the remote server which downloads the diagnosis or interpretation to the computing device. Alternatively or in combination, the application loaded onto the computing device may automatically provide the diagnosis or interpretation. The diagnosis or interpretation may comprise a diagnosis for atrial fibrillation, an arrhythmia, or the like and/or a risk level for such conditions.

A system for performing the method 800 may comprise at least a computing device for one or more users and a remote server or a cloud-based service for managing the physiological parameter(s) acquired through the computing device. The computing device may include on-board sensors for acquiring the physiological parameter signals. For example, the computing device may include a plurality of electrodes for acquiring various physiological parameter signals (e.g., ECG, EEG, EMG, body fat percentage, skin hydration, etc.) or imaging and light sources for acquiring various physiological parameter signals (e.g., heart rate, blood oxygenation levels, blood glucose levels, etc.) Alternatively or in combination, the system may further comprise an accessory in communication (wireless (e.g., Bluetooth, Bluetooth LE, NFC, WiFi, ZigBee, ultrasound, or the like) or wired (e.g., USB, lightning, audio port, or the like)) with the computing device and the accessory may include sensor components as described herein for measuring the physiological parameter(s) which are subsequently sent to the computing device. Users may access the remote server or cloud-based service through the computing device or through another computing device for many purposes. For example, the user may archive his or her physiological parameter signals, view the archived physiological parameter signals, or view analyses, interpretations, or diagnoses of the physiological parameter signals. Access to the remote server or cloud-based service may be provided to a select group of medical professionals which may provide the analyses, interpretations, or diagnoses of the user physiological signals. Alternatively or in combination, the physiological parameter signals from a plurality of users may be pooled together to generate population statistics which may be studied to improve the analyses, interpretation, or diagnoses of the users. For example, the system may further comprise a machine learning platform configured to learn from the population data to better identify disease(s) or risk for diseases(s) from the user provided physiological parameter signals.

Although the above steps show the method 800 of monitoring a physiological parameter in accordance with many embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the treatment.

One or more of the steps of the method 800 may be performed with circuitry as described herein, for example, one or more of a processor or logic circuitry (e.g., of a computing device or accessory thereof) such as a programmable array logic for a field programmable gate array or a application specific integrated circuit. The circuitry may be programmed to provide one or more of the steps of the method 800, and the program may comprise program instructions stored on a computer readable memory or programmed steps of the logic circuitry such as the programmable array logic or field programmable gate array, for example.

While the filtering methods described herein are described for filtering ECG signals, one skilled in the art would appreciate that the signal filtering methods may be applied for other physiological signals, including but not limited to electroencephalogram (EEC) signals, electromyogram (EMG) signals, mechanomyogram (MMG) signals, electroculograpm (EOG) signals, galvanic skin response (GSR) signals, magnetoencephalogram (MEG) signals, or other biosignals.

In general, any of the apparatuses or modules described herein may be hardware, software, and/or firmware. In particular, these apparatuses may be software base apparatuses, including programs (e.g., application programs/software) for execution on one or more general or dedicated microprocessors.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present disclosure.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure and inventions described therein. It should be understood that various alternatives to the embodiments of the disclosure described herein may be employed in practicing the disclosure and the inventions described therein. It is intended that the following claims define the scope of the invention and that methods and structures within the scope of these claims and their equivalents be covered thereby.

What is claimed is:

1. An ECG sensing computing device, comprising:
a processor;
one or more electrodes configured to measure an ECG signal; and
a non-transitory computer readable storage medium encoded with a computer program including instructions executable by the processor to cause the processor to:
receive the ECG signal;
filter the ECG signal by applying a first filtering stage;
apply a second filtering stage; and
apply a third filtering stage to the ECG signal, wherein the third filtering stage comprises removing low-amplitude, high frequency noise; and wherein the first, second, and third filtering stages are different from one another.

2. The device of claim 1, wherein the computer program includes instructions that cause the processor to display the filtered ECG signal in real-time as the ECG signal is received and filtered, and wherein the displayed filtered ECG signal has improved readability such that a medical professional can better diagnose the filtered ECG signal.

3. The device of claim 1, wherein the computer program includes instructions that cause the processor to perform the first, second, and third filtering stages in sequence.

4. The device of claim 1, wherein the computer program includes instructions that cause the processor to perform the first, second, and third filtering stages are in parallel.

5. The device of claim 1, wherein the first filtering stage comprises removing baseline wander of the ECG signal.

6. The device of claim 5, wherein removing the baseline wander comprises removing a moving average of the ECG signal from a portion of the ECG signal.

7. The device of claim 1, wherein the second filtering stage comprises removing high-frequency noise from the ECG signal.

8. The device of claim 7, wherein removing the high-frequency noise comprises applying a Savitzky-Golay de-noising filter to smooth the ECG signal.

9. The device of claim 8 wherein applying the Savitzky-Golay de-noising filter comprises applying a high order Savitzky-Golay filter to a QRS segment of the ECG signal and applying a low order Savitzky-Golay filter to a non-QRS segment of the ECG signal.

10. The device of claim 1, wherein the third filtering stage comprises removing low-amplitude, high frequency noise from the ECG signal.

11. The device of claim 10, wherein removing the low-amplitude, high frequency noise from the ECG signal comprises applying threshold fit smoothing to the ECG signal.

12. The device of claim 1, wherein the computer program includes instructions that cause the processor to pre-process the received ECG signal before filtering the ECG signal.

13. The device of claim 12, wherein pre-processing the received ECG signal comprises applying user-selected mains filter.

14. The device of claim 1, wherein the computer program includes instructions that cause the processor to detect an amount of noise of the received ECG signal.

15. The device of claim 14, wherein the computer program includes instructions that cause the processor to vary an amount of filtering applied to the received ECG signal in response to the amount of noise detected.

16. The device of claim 15, wherein detecting the amount of noise comprises training a module of a computing device with a noise model.

17. The device of claim 1, wherein the computer program includes instructions that cause the processor to vary an amount of filtering applied to the received ECG signal in response to user input.

18. A computing device for processing an electrocardiogram (ECG) signal of a user to provide improved readability of the ECG signal for a medical professional in diagnosing the ECG signal, the device comprising:
a processor;
one or more electrodes configured to measure an ECG signal; and
a non-transitory computer readable storage medium encoded with a computer program including instructions executable by the processor to cause the processor to:
receive the measured ECG signal;
filter the received ECG signal;
display the filtered ECG signal on a display of the computing device; and
vary an amount of filtering applied to the displayed ECG signal in response to user input, wherein the amount of filtering is varied in real-time as the ECG signal is displayed, and wherein the displayed filtered ECG signal has improved readability such that a medical professional can better diagnose the filtered ECG signals.

19. The device of claim 18, wherein the ECG signal is displayed in real-time as the ECG signal is provided and filtered.

20. The device of claim 18, wherein to filter the received ECG signal comprises applying a first filtering stage, a second filtering stage, and a third filtering stage to the provided ECG signal, wherein the first, second, and third filtering stage are different from one another.

21. The device of claim 18, wherein the computing device comprises one or more of a smartphone, a tablet computer, a laptop computer, a personal computer, a personal digital assistant, or a wearable computer.

22. A computing device for processing an electrocardiogram (ECG) signal of a user, the device comprising:
a processor;
one or more electrodes configured to measure an ECG signal; and
a non-transitory computer readable storage medium encoded with a computer program including instructions executable by the processor to cause the processor to:
receive the measured ECG signal;
pre-process the received ECG signal; and
filter the pre-processed ECG signal by (i) removing baseline wander of the ECG signal, (ii) removing high frequency noise from the ECG signal, and (iii) removing low- amplitude, high frequency noise from the ECG signal, wherein steps (i) to (iii) are performed sequentially.

* * * * *